United States Patent
Liu

(10) Patent No.: US 11,452,317 B2
(45) Date of Patent: *Sep. 27, 2022

(54) POSTURE CORRECTION BRA

(71) Applicant: IFGCURE HOLDINGS, LLC, Los Angeles, CA (US)

(72) Inventor: Stephen H. Liu, Los Angeles, CA (US)

(73) Assignee: IFGCURE HOLDINGS, LLC., Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/845,728

(22) Filed: Apr. 10, 2020

(65) Prior Publication Data

US 2020/0237028 A1 Jul. 30, 2020

Related U.S. Application Data

(60) Division of application No. 16/125,453, filed on Sep. 7, 2018, now Pat. No. 10,721,975, which is a continuation-in-part of application No. 16/057,558, filed on Aug. 7, 2018, now abandoned, which is a continuation-in-part of application No. 16/029,567, filed on Jul. 7, 2018, now abandoned.

(60) Provisional application No. 62/649,542, filed on Mar. 28, 2018.

(51) Int. Cl.
*A41C 3/00* (2006.01)
*A41C 3/08* (2006.01)
*A61F 5/02* (2006.01)
*A41F 15/00* (2006.01)

(52) U.S. Cl.
CPC .............. *A41C 3/0064* (2013.01); *A41C 3/08* (2013.01); *A41F 15/00* (2013.01); *A61F 5/026* (2013.01); *A41B 2300/22* (2013.01); *A41B 2400/32* (2013.01)

(58) Field of Classification Search
CPC ....... A41C 3/0064; A41C 3/08; A41C 3/0057; A41C 1/02; A41C 1/0014; A41C 1/0028; A41B 2400/32; A41B 2300/22; A61F 5/024; A61F 5/026; A61F 5/028; A41F 15/00
USPC ......................................... 128/873, 874, 875
See application file for complete search history.

(56) References Cited

U.S. PATENT DOCUMENTS 245,524 A * 8/1881 Lubin ...................... A61F 5/026
    2/45
1,293,089 A * 2/1919 Hardy ..................... A61F 5/028
    2/44

(Continued)

*Primary Examiner* — Jocelyn Bravo
(74) *Attorney, Agent, or Firm* — Ferguson Case Orr Paterson

(57) ABSTRACT

A therapeutic posture correcting bra and method of manufacture thereof in the posture re-balance, shoulder and spine muscle rebalance, posture correction, occupation risk prevention, anti-aging, and athletic enhancement space. A bra that is uniquely designed, manufactured and fabric woven for proprioceptive posture rebalance, correction and athletic enhancement that allows for breathability, functionality, range of motion, and fashionability. The therapeutic posture correcting bra is uniquely designed and narrows the distance between shoulder blades from proprioceptive muscle retraction at least 5 mm secondarily providing shoulder and spine muscle activation and relaxation for improved physical wellness.

10 Claims, 17 Drawing Sheets

(56) References Cited

U.S. PATENT DOCUMENTS

| | | | |
|---|---|---|---|
| 1,766,278 A * | 6/1930 | Bollwine | A41C 3/00 450/83 |
| 2,581,036 A * | 1/1952 | McIlhinney | A41F 1/006 450/2 |
| 2,591,462 A * | 4/1952 | Mungo | A41C 3/00 450/2 |
| 4,202,327 A | 5/1980 | Glancy | |
| 4,957,103 A | 9/1990 | Young | |
| 5,109,546 A * | 5/1992 | Dicker | A63B 21/4025 2/70 |
| 5,158,531 A | 10/1992 | Zamosky | |
| 5,451,200 A | 9/1995 | LaBella | |
| 5,599,286 A | 2/1997 | LaBella | |
| 5,718,670 A | 2/1998 | Bremer | |
| 5,823,851 A * | 10/1998 | Dicker | A41C 3/02 450/2 |
| 5,873,767 A * | 2/1999 | Pickett | A41C 3/08 450/1 |
| 6,068,538 A * | 5/2000 | Alleyne | A41C 3/0057 450/1 |
| 6,102,879 A | 8/2000 | Christensen | |
| 6,213,922 B1 | 4/2001 | Ivanovich | |
| 6,440,094 B1 | 8/2002 | Maas | |
| 6,676,617 B1 | 1/2004 | Miller | |
| 6,846,217 B1 * | 1/2005 | Struble | A41C 3/08 2/78.1 |
| 6,846,219 B2 * | 1/2005 | Moyer | A41C 3/00 450/39 |
| 6,860,789 B2 * | 3/2005 | Bell | A41C 3/0064 2/102 |
| 6,936,021 B1 | 8/2005 | Smith | |
| 7,134,969 B2 | 11/2006 | Citron | |
| 7,153,246 B2 | 12/2006 | Koscienly | |
| 7,395,557 B1 | 7/2008 | Ledyard | |
| 7,662,121 B2 | 2/2010 | Zours | |
| 7,871,388 B2 | 1/2011 | Brown | |
| 8,047,893 B2 | 11/2011 | Fenske | |
| 8,083,693 B1 | 12/2011 | McKeon | |
| 8,308,670 B2 | 11/2012 | Sandifer | |
| 8,516,614 B2 | 8/2013 | Karasina | |
| 8,556,840 B2 | 10/2013 | Burke | |
| 8,795,213 B2 | 8/2014 | Mills | |
| 8,795,215 B2 | 8/2014 | Rossi | |
| 8,887,315 B2 | 11/2014 | Boynton | |
| 8,905,956 B2 | 12/2014 | Waeger | |
| 8,910,317 B2 | 12/2014 | Decker | |
| 8,932,236 B1 | 1/2015 | McKeon | |
| 9,009,863 B2 | 4/2015 | Decker | |
| 9,167,854 B2 | 10/2015 | Levian | |
| 9,168,167 B2 | 10/2015 | Brown | |
| 9,226,534 B2 | 1/2016 | Puni | |
| 9,439,459 B2 | 9/2016 | Placanica | |
| 9,445,932 B2 | 9/2016 | Boynton | |
| 9,456,919 B2 | 10/2016 | Pollack | |
| 9,504,280 B2 | 11/2016 | Levian | |
| 9,883,703 B2 | 2/2018 | Schultz | |
| 9,931,236 B2 | 4/2018 | Williamson | |
| 2004/0107479 A1 | 6/2004 | Dicker | |
| 2005/0197607 A1 | 9/2005 | Brown | |
| 2006/0000478 A1 | 1/2006 | Taylor | |
| 2006/0025039 A1 * | 2/2006 | Barbour | A41D 1/18 450/1 |
| 2008/0134409 A1 | 6/2008 | Karasina | |
| 2009/0062704 A1 | 3/2009 | Brown | |
| 2010/0005569 A1 * | 1/2010 | Sanders | A41C 3/0057 2/400 |
| 2010/0019227 A1 | 1/2010 | Wasshuber | |
| 2011/0213283 A1 | 9/2011 | Brown | |
| 2012/0174282 A1 | 1/2012 | Newton | |
| 2012/0078149 A1 | 3/2012 | Azimzadeh | |
| 2012/0122370 A1 * | 5/2012 | Heath | A41C 3/0057 450/80 |
| 2013/0047313 A1 | 2/2013 | Windisch | |
| 2013/0053744 A1 | 2/2013 | Convert | |
| 2013/0090521 A1 | 4/2013 | Lau | |
| 2013/0103079 A1 | 4/2013 | Lau | |
| 2014/0058307 A1 | 2/2014 | Marshall | |
| 2014/0100501 A1 | 4/2014 | Burke | |
| 2014/0221893 A1 | 8/2014 | Modglin | |
| 2015/0040286 A1 | 2/2015 | Schultz | |
| 2016/0044971 A1 * | 2/2016 | Randall | A41C 3/0057 450/39 |
| 2017/0360118 A1 * | 12/2017 | Randall | A41C 3/02 |

* cited by examiner

POSTURE CORRECTION BRA

CROSS REFERENCE TO RELATED APPLICATIONS

This application is a divisional of U.S. patent application Ser. No. 16/125,453 entitled POSTURE RECOVERY THERAPEUTIC BRA filed on Sep. 4, 2018, which is a continuation-in-part application of U.S. patent application Ser. No. 16/057,558 entitled POSTURE, PERFORMANCE, RECOVERY (PPR) BRA filed on Aug. 7, 2018, which is a continuation-in-part application of U.S. patent application Ser. No. 16/029,567 entitled POSTURE, PERFORMANCE, RECOVERY (PPR) BRA filed on Jul. 7, 2018, which claims priority to U.S. Provisional Patent Application No. 62/649,542, entitled POSTURAL RECOVERY BRA, filed Mar. 28, 2018. The contents of all applications are hereby incorporated by reference in their entirety.

FIELD OF THE INVENTION

The present invention is directed to a therapeutic posture correcting bra for improved muscle re-balance, posture correction, therapeutic anti-slouching body habitus, improved aging slouching, occupation risk prevention and better productivity, and athletic enhancement. The inventive bra is uniquely designed and comprises a woven mesh-strap fabric configuration for proprioceptive posture rebalance, correction and athletic enhancement while allowing for breathability, functionality, range of motion, and fashion. The inventive bra is uniquely designed and narrows the distance between shoulder blades from proprioceptive retraction and allow therapeutic solutions for women health.

BACKGROUND OF THE INVENTION

Posture correcting garments are known and have been used in for several years in proprioceptive therapy; primarily with a goal of stimulating body muscles into better alignment and posture resulting in a slight S-shape of the spine—the orthopedic posture gold standard. The importance of having good posture is a well-known and a long-accepted priority among healthcare professionals and even non-experts in the field. Good posture is vital for overall health (prevention of back, shoulder, neck pain, etc.) and vital for athletic performance; as poor posture or form during dynamic athletic activities results in inefficient biomechanics and body movement. Poor posture is typically observationally categorized by 'shoulders rolled forward', 'a forward curvature in the thoracic spine', and/or a 'left or right lean of the thoracic spine. In addition, inefficient body movement caused by poor posture prevents full utilization of skeleto-muscular range of motion and strength which commonly causes repetitive injury. Typical treatment methods for those suffering from back, neck, and other pain include chiropractic or other physical therapy or orthopedic surgeon evaluation and possible treatment. Such medical procedures to correct poor posture involve injections, medications, rehabilitation, and typically as a last resort—surgical correction. As many cannot afford the cost nor time of extensive and costly chiropractor or physical therapy treatment (either short term or long-term treatment), there exists a great need for affordable methods and systems to correct and maintain the proper posture of individuals to provide and maintain:
   a) correct functional anatomy,
   b) improved muscle efficiency,
   c) improved pain relief with minimal discomfort to users, and
   d) creation of good habits so individuals do not develop poor-posture related pain in the first place.

The first attempts using a wearable garment to refine biomechanical factors that influence posture and kinesthetic states was originated in the 1970's within the Soviet space program, in order to counteract the effects of long-term weightlessness. This device, known as the Adeli suit, is used to treat pediatric patients with postural disabilities due to neurological conditions that lead to brain damage or spinal cord injury. Its design is relatively simple, involving elastic connections between the primary joints, specifically to target positions of antagonistic muscle pairs. However, there are still many other of ways and degrees to which the body can become imbalanced due to disruptions in the kinetic chain of muscle activation.

Muscles devoted substantially to the concepts of balance and posture are sometimes referred to as gravity and anti-gravity muscles; they are the tools that provide upright organisms with the ability to maintain the center-of-gravity (COG) within a stable base of support. Upright balance is attained when a vertical line follows from the center-of-gravity, directly down through this base of support. Any imbalance will cause compensatory abnormalities which will affect alignment within the body's whole musculoskeletal system. Optimized postural alignment is crucial in counteracting the constant downward gravitational forces opposing the body. When the upright force of musculoskeletal architecture and the downward force of gravity are balanced, muscles are able to function with the least amount of work, i.e. peak efficiency.

When the upright body holds better posture, smaller amounts of stress and strain are placed on the muscles, ligaments and bones thereby enhancing their efficiency and increasing bone density and muscle mass in the long term. Opposing the force of gravity, the so called anti-gravity muscles assist to maintain an upright, balanced posture. For the lower body, these muscles consist of namely the soleus muscles, the extensors of the leg, the gluteus maximus, the quadriceps femoris. For the upper body and the muscles of the back, these muscles include the trapezius, the rhomboids, and several smaller groups around the shoulder such as the teres minor and subscapularis. Additionally, the cervico-occipital muscle groups maintain the head in an erect position, thereby preventing it from rolling forward. These muscle groups simultaneously play an important role in the proprioception process, with proprioceptors in the dermal surface sending key information about pressure in the feet to the antigravity muscles through the nervous system. Any weakening of these muscles combined with the continuously working gravitational forces leads to poor postural stability, which affects muscle function. If left untreated, this ultimately leads to degeneration of joints and deformities such as a structural collapse in the foot. Postural alignment is essential to maintain normal length-tension relationships of the muscles especially during dynamic posture, determining the ease with which the body segments align themselves throughout movement. Any disruption to this alignment throws the kinetic chain of the body off balance, making the person susceptible to a host of injuries. Understanding our limitations at controlling the effect gravitational forces have on the muscles and structure should form the basis of treatment programs As one treatment option, posture shirts and girdles were created to fill the burgeoning need of postural correction. Posture shirts and girdles typically contain vertical straps that do not mimic natural anatomical movement. These vertical straps take the wrong approach to correcting a wearer's posture, namely that the straps do not focus on proprioceptive correction to achieve natural postural alignment but instead focus on force. This force creates an unnatural alignment that may push a wearer's shoulders backwards in an outward appearance of better posture but in reality, doesn't achieve much short term or long-term success. Natural posture alignment in the thoracic spine is achieved when posterior muscle groups (i.e., trapezius, rhomboids, latissimus dorsi) and anterior muscle groups (serratus anterior, etc.) are both exerting the same amount of force, thus allowing the body to be balanced. Therefore, garments created in this space targeted this natural (proprioceptive) balancing; however, these garments were not able to fully achieve this goal due to several limitations, including the one listed above.

Further to this idea, the vertical straps that these companies utilize end at the bottom of the buttocks, contributing to the unnatural pull that forces the shoulders back into an improper and unnatural position that does not mimic natural anatomical movement. The corresponding picture would be someone grabbing the bottom of one's shirt from the back and pulling it downwards and tucking it underneath one's glutes; this would certainly force one's shoulders back and posture to be straightened but it would also align the posture in the incorrect form and prove to be extremely uncomfortable. For instance, one shirt of this kind was made from a cotton body with elastic straps that were attached at the front of each shoulder, ran over the back parallel to the spine, and connected at the bottom seam. That same shirt was not only anatomically incorrect, it was also extremely tight (made from a LYCRA® spandex fiber material), thus not breathable and uncomfortable. The construction method required also led to these shirts needing to be full-length, which can get hot and sweaty.

Known methods and systems include US20090062704 and US20110213283 directed to a shirt type garment made from a cotton body with elastic straps attached at the front of each shoulder and running over the back parallel to the spine and connected at a seam toward the bottom of the shirt. These shirts are made from a LYCRA® spandex fiber material with mesh and a woven stretch fabric. Similar systems utilize a LYCRA® spandex fiber combination material to provide structural stability, compression, and an athletic garment look. However, such material is not breathable. In order to effectively gain stability from and in the body for proprioception, and to correct posture imbalance; LYCRA® spandex fiber garments must be worn extremely tight to the body leading to discomfort.

Not only does LYCRA® spandex fiber material require an extremely tight wear from the user, it's also unsightly and unfashionable and does not translate well to commercial use, since customers are not inclined to wear the garment as their only layer. By wearing an additional layer on top of the LYCRA® spandex fiber to cover the unsightly artificial material layer of the posture correction garment, the breathability issue is compounded with an additional layer of tightness. Due to this combination, individuals typically stop wearing LYCRA® spandex fiber made posture shirts, thus sabotaging the process of building good habits in postural alignment. All of these issues compound to discourage patient wear and compliance since each factor adds an additional negative feature.

One therapeutic method for correcting posture involves the body's proprioceptive sense. An organism uses proprioception to maintain an internal model of its body's orientation in space, a sort of mental avatar representing the mind's best guess as to how its physical limbs are moving. When the primary motor cortex signals the muscles to fire, it also emits an efference signal, also known as a corollary discharge. This second signal has been hypothesized to suppress the subsequent firing of sensory cortex networks when they are inevitably stimulated by the aforementioned motor movement. Therapeutically applied proprioception can be explained by intensifying and subsequently normalizing the afferent proprioceptive mobility-controlling input.

Rather than utilizing vertical straps, one form of the proprioceptive correction technique is the utilization of horizontal straps that contract the rhomboids and the upper trapezius in a horizontal motion that moves the scapula towards the spine and is thus anatomically correct. This natural postural correction is effective because it physically (through the anatomically correct means) corrects a wearer's posture and then passively influences the posture after it is corrected. This is achieved due to the natural tension that the horizontal straps exert on the wearer, which makes it so that the wearer wants to be in postural correct form without the force of a vertical strap constantly pulling over the shoulder and down to the buttocks region.

Additional systems include U.S. Pat. Nos. 4,202,327, 4,957,103, 5,158,531, 5,451,200, 5,599,286, 5,718,670, 6,102,879, 6,213,922, 6,440,094, 6,676,617, 6,936,021, 7,134,969, 7,153,246, 7,395,557, 7,662,121, 7,871,388, 8,047,893, 8,083,693, 8,308,670, 8,516,614, 8,556,840, 8,795,213, 8,795,215, 8,887,315, 8,905,956, 8,910,317, 8,932,236, 9,009,863, 9,167,854, 9,168,167, 9,226,534, 9,439,459, 9,445,932, 9,456,919, 9,504,280, 9,883,703, 9,931,236, US20040107479, US20050197607, US20060000478A1, US20080134409A1, US20090062704, US20100192274A1, US20120078149, US20120174282, US20130047313, US20130053744, US20130090521, US20130103079, US20140058307, US20140100501, US20140221893 and US20150040286A1.

However, none of the prior art references provide a proprioceptive bra that efficiently and effectively corrects a wearer's posture. None of the prior art references provided data for narrowing of the distance between the shoulder blades in a resting position or narrowing of the distance between the scapula to the spinous process, using a bra. There exists a need for a more proprioceptive woven fabric posture re-balance bra that corrects a wearer's posture, by narrowing the distance between right and left scapula using proprioceptive muscle retraction, using anatomically correct movement that allows for shoulder mobility, is breathable and aesthetically pleasing to promote patient compliance, and is not so tight as to be hot and uncomfortable to wear.

Accordingly, the present invention is directed to solving all of these problems.

SUMMARY OF THE INVENTION

It is an object of the present invention to provide a proprioceptive bra that efficiently corrects a wearer's posture. It is an object of the present invention to provide a proprioceptive bra that brings both shoulder blades (scapula) closer to the spine, or closer together, that corrects a wearer's posture.

It is an object of the present invention to provide a comfortable and proprioceptive woven fabric posture re-balance bra that corrects a wearer's posture using anatomically correct movement that allows for shoulder mobility, is breathable and aesthetically pleasing to promote patient compliance, and is not so tight as to be hot and uncomfortable to wear.

It is an object of the present in invention to be commercially successful, and to be both functional and fashionable (or at least, not unsightly); and to successfully reach a wide swath of users who may need such therapy to prevent or assist in correcting present and/or future thoracic, lumbar, shoulder, etc. pain, and spectrum ranges from occupation risk prevention seen in many industries, and professionals, teen age girls, and aging.

Objects of the invention are achieved by providing a stylish comfort therapeutic posture correcting bra, comprising a front portion; a first strap, the first strap configured in an approximate C-shape including a two-way stretch fabric, the first strap attached to the front portion of the posture correcting bra at one end of the first strap; a second strap, the second strap configured in an approximate C-shape including a two-way stretch fabric, the second strap attached to the front portion of the posture correcting bra at one end of the second strap; a variable tension poly elastic strap that provides horizontal tension and sits between the first strap and the second strap; a chest pre-tension poly-elastic strap band comprising two-way stretch fabric, the chest band attached to the poly elastic strap and the two side seams; and an expansion elastic sewn into the chest band, the expansion elastic configured to limit 360-degree compression of the chest band. The C shape configuration also creates a C shape area (both on the right and left side of the posterior shoulder) which encompasses the entire mass of the scapula along all its borders for better muscle proprioception. Power mesh is sandwiched in the C shape band, configured in the front inner bra, and in the back bra, and the power mesh can be embedded in variety of combination i.e. C strap only, front bra only, back bra only, or a combination of all or part of the above.

Other objects of the invention are achieved by providing a therapeutic posture correcting bra, comprising: a front portion; a first strap, the first strap configured in an approximate C-shape including a two-way stretch fabric, the first strap attached to the front portion of the posture correcting bra at one end of the first strap; a second strap, the second strap configured in an approximate C-shape including a two-way stretch fabric, the second strap attached to the front portion of the posture correcting bra at one end of the second strap; a variable tension poly elastic strap that provides horizontal tension, the variable tension poly elastic strap comprises at least one horizontal poly elastic strap pretensioned and with a various width pending on the size of the wearer (usually one to four inches); and a mesh layer provided underneath the variable tension poly elastic strap. The mesh layer is also provided as single or double lining of the entire bra or partial bra, or just in C strap.

In certain embodiments, the at least one horizontal poly elastic strap is located between the first strap and the second strap.

In certain embodiments, the variable tension poly elastic strap comprises at least two horizontal spaced apart poly elastic straps between the first strap and the second strap. In certain embodiments, the variable tension poly elastic strap comprises at least three horizontal spaced apart poly elastic straps between the first strap and the second strap.

In embodiments, at least one horizontally spaced pretensioned elastic strap is provided. In certain embodiments, the at least one horizontally spaced pretensioned elastic strap. The strap is either sewn in to the exterior or interiorly within the bra. The posterior elastic strap mesh integration can be sewn into any existing bra. The C strap posterior elastic mesh integration can be integrated into any existing front panel bra, or suitable bra.

In certain embodiments, the C-shape of the first strap and the C-shape of the second strap form an approximate X-shape configuration with the opposing's C's that form the shape can be touching or intersecting across the back of a wearer.

In certain embodiments, the C-shape of the first strap and the C-shape of the second strap oppose one another, such the first strap and the second strap each have the C-shape facing away from a center of the wearer's back. In certain embodiments, the C-shape of the first strap and the C-shape of the second strap are configured to primarily retract the shoulder blades and secondarily expand the rib cage for ease of breathing and comfort fit of a user. The C shape strap lie along the borders of the scapula and embodies the entire scapula fossa for better proprioception and movements of the scapula.

In certain embodiments, the first upper poly elastic strap is disposed between the upper sections of the C-shaped straps and the lower poly elastic strap is disposed between the lower sections of the C-shaped straps.

In certain embodiments, the first strap and the second strap each include a side seam that facilitates and supports the S curve of the wearer's spine.

In certain embodiments, the poly elastic strap is configured to pull a wearer's thoracic towards the anterior of the wearer, thus opening up the ribcage of the wearer for ease of breathing and comfort of fit.

In certain embodiments, the poly elastic strap is configured to provide a see-saw motion resulting in an improved scapular proprioceptive retraction and secondarily rib cage expansion for better breathing.

In certain embodiments, the expansion elastic located in the lateral portions of the chest combine with the poly elastic strap to simultaneously allow for expansion of the ribcage during inhalation as well as the pulling of the scapula back into proper alignment, which allows an easier fit while still maintaining proper postural correction.

In certain embodiments, the posterior poly elastic strap comprises one or more of nylon, TENCEL® lyocell fiber and spandex. In certain embodiments, the poly elastic strap comprises between about 65% and about 90% nylon, between about 5% and about 20% TENCEL® lyocell fiber, and between about 5% and about 20% spandex. In certain embodiments, the poly elastic strap comprises about 80% nylon, about 10% TENCEL® lyocell fiber, and about 10% spandex. In certain embodiments, the posterior poly elastic strap can be any mixture of fabric. The power mesh can be of any combined materials, synthetic or non-synthetic.

In certain embodiments, the bra comprises one or more poly elastic straps. In certain embodiments, the bra comprises a plurality of variable tension poly elastic straps disposed one above the other.

In certain embodiments, the poly elastic strap comprises a first upper poly elastic strap and a second lower poly elastic strap. In certain embodiments, the first upper poly elastic is disposed between the upper sections of the C-shaped first strap and second strap. In certain embodiments, the second lower poly elastic strap is disposed between the lower sections of the C-shaped first and second straps.

In certain embodiments, the bra comprises three or more horizontal variable tension poly elastic straps. In certain embodiments, the bra comprises four or more, or five or more horizontal variable tension poly elastic straps. In certain embodiments, the bra comprises variable tension poly elastic straps constructed in an X-shape configuration. In certain embodiments, the bra comprises a plurality of horizontal variable tension poly elastic straps and variable tension poly elastic straps constructed in an X-shape configuration. In certain embodiments, the horizontal poly elastic straps disposed above the X-shape configuration poly elastic straps. In certain embodiments, the elastic straps can be positioned to range from a superior angle of the scapular to the inferior angle of the scapula.

In certain embodiments, in use, the poly elastic straps extend between about, or below about the nucha and the center of the back of a wearer. In certain embodiments, in use, the poly elastic straps lay along, and/or aside the scapula of a wearer, from top to bottom.

In certain embodiments, the poly elastic straps are provided when maximally stretched, i.e., in a pre-tensioned state.

In certain embodiments, the second strap provides posterior pull to the bra wearer and places the bra wearer's ribcage into proper alignment by providing horizontal stretch and pulling towards the center of the wearer's spine.

In certain embodiments, the poly elastic strap provides pull posterior to the bra wearer and places the bra wearer's ribcage into proper alignment by providing horizontal stretch and pulling towards the center of the wearer's spine In certain embodiments, the front portion of posture correcting bra includes two cup portions, the two cup portions able to provide support for the wearer's breasts.

In certain embodiments, the bra provides support to the wearer. In certain embodiments, the chest band combined with the poly elastic PPR strap has a width and tension that is varied to impact the degree of adjustment to the wearer's posture.

In certain embodiments, the first strap and the second strap each have a width within the range of between about 1-4 inches. In certain embodiments, the first strap and the second strap can be of various width depending upon the size of a wearer. In certain embodiments, the width is pretensioned with similar width.

In certain embodiments, the bra contains a poly-elastic strap that acts as a proprioceptive mechanism to correct a wearer's posture. In certain embodiments, the chest band and the expansion elastic are located beneath both armpits of the wearer. In certain embodiments, correction of a wearer's posture is corrected proprioceptively. In certain embodiments, the bra corrects a wearer's posture by retracting the shoulder of the wearer to the posterior, thus placing the scapula in the proper anatomical location.

In certain embodiments, the bra improves athletic performance.

In certain embodiments, the bra contains anti-microbial moisture wicking and protects against ultra-violet (UV) rays, and in combination with synthetic or non-synthetic materials.

In certain embodiments, the bra includes side panels and wherein the side panels help distribute lower force across the wearer's ribcage. In certain embodiments, the bra is form-fitting and designed to conform to the wearer's body.

In certain embodiments, the first strap includes a lower section and an upper section, wherein the upper section of the first strap provides greater force upon the wearer than the lower section of the strap. In certain embodiments, the second strap includes a lower section and an upper section, wherein the lower section of the second strap provides greater force upon the wearer than the upper section of the second strap.

In certain embodiments, the upper sections connect to the chest portion of the bra. In certain embodiments, the upper section extends between a top end of the front portion and about a central location of the C-shape. In certain embodiments, the lower section extends between the central location of the C-shape and a side end of the front portion. In certain embodiments, in use, the upper section positioned to extend from the shoulder to a location proximate the C7-T3 vertebrae of a wearer's spine, corresponding to the superior angle of the scapula. In certain embodiments, the position of the upper section improves proprioceptive retraction. In certain embodiments, in use, the lower section positioned to extend from the location proximate the T6-T8 vertebrae to a location proximate the inferior angle of the scapula. In certain embodiments, the position of the lower section provides improved expansion to the rib cage allowing better inhalation. In certain embodiments, the upper sections overlay a length of the rhomboids and/or upper trapezius of a wearer's back.

In certain embodiments, the lower sections of the first strap and the second strap each include a side seam that connects between the front portion and the back portion.

In certain embodiments, the first strap and the second strap each include a middle seam connecting the lower section to the upper section.

In certain embodiments, the bra further includes a single or double mesh layer provided underneath the poly elastic strap portion and configured to provide improved shoulder retraction and comfort to the wearer.

In certain embodiments, the mesh body is manufactured from a material chosen from the group consisting of nylon, spandex, cotton, polyester, chiffon, denim, lace, leather, wool, or a combination thereof, not excluding synthetic or non-synthetic materials.

In certain embodiments, the bra corrects the wearer's posture by narrowing the distance between the left and right scapula. In certain embodiments, the distance narrowing between the left and right scapula is of at least 5 mm.

In certain embodiments, the front portion of the bra is detachable and interchangeable from the first strap and the second strap. In certain embodiments, the front portion of the bra includes multiple styles, mesh layering, and includes customizable options.

In certain embodiments, the chest band allows for ease of breathing and a more comfortable fit.

In certain embodiments, the chest band allows for improved expansive movement of the rib cage.

In certain embodiments, the chest band is a poly-elastic strap that creates retraction towards the spine while also acting as a proprioceptive mechanism to correct a wearer's posture In certain embodiments, the bra assists the wearer with scapula rebalance. In certain embodiments, the bra prevents hyper flexion-extension of a rotator cuff of a wearer. In certain embodiments, the bra prevents damage of the scapular rotators, spinal muscles of the wearer. In certain embodiments, the side seams support the curve of the back to allow for forward and backward movement involving the shoulder blades, spine, and the ribcage.

In certain embodiments, the posterior portion of the bra can be configured to be integrated to a secondary bra via at least one integrated intersection.

In certain embodiments, the bra provides postural support to a wearer suffering from less than ideal posture, or suffering a related malady selected from the following group consisting of: rounded shoulders, scapular dyskinesis, kyphosis, forward head, lordosis, scoliosis, rounded shoulder from cervical spine injury, rotator cuff tears, shoulder pathologies, pregnancy, large dense breast women with chronic round shoulders, aging posture, neck pathologies, chronic headaches, acromioclavicular joint separation, arthritis, and general posterior musculature weakness, shoulder muscle rebalance, shoulder rehabilitation, shoulder recovery, shoulder training, scapula rebalance muscular tension rebalance, cervical/occipital neuralgia, frozen shoulder, scapular winging.

In certain embodiments, the bra corrects the wearer's posture through a form of direct physical therapy and indirectly through proprioceptive feedback. In certain embodiments, the bra can be sewn or attached into any existing shirt or dress or come pre-sewn in the production pipeline.

In certain embodiments, the poly elastic strap is designed to relieve all tension in the bra when the wearer is standing or sitting with correct postural alignment, and wherein the variable tension poly-elastic strap ceases posterior pull.

In certain embodiments, the bra allows for a full range of motion for the wearer and the restriction of movement is minimized. In certain embodiments, the bra corrects musculoskeletal realignment, which in turn improves blood circulation in the wearer. In certain embodiments, the bra improves athletic performance.

Other objects of the invention are directed to a new design, innovative method of manufacturing a therapeutic posture correcting bra.

Other objects of the invention are directed to a bra device having an opposing-C-shape with a poly-elastic strap that provides an anchor point for posture correction, retracting shoulder blades closer to the spine; and includes woven "no stretch" nylon and/or TENCEL® lyocell fiber spandex, and in combination of variable fabrics.

In certain embodiments, the inventive garment also includes a detachable back and front to provide greater customization Other objects of the invention are achieved by providing a garment device for correcting a user's posture, the garment device comprising: an opposing C construction with woven fabric, one or more upper straps, chest band, expansion elastic, side seams, and poly elastic strap on the back.

In certain embodiments, correction of a wearer's posture is corrected proprioceptively by muscle retraction of scapula. In certain embodiments, the garment corrects a wearer's posture. In certain embodiments, at least one variable tension poly elastic strap provides support to the wearer.

In certain embodiments, the garment corrects the wearer's posture by retracting the shoulder blades, essentially move the head to a posterior position, less tension on the neck muscles, and placing the scapula in the proper anatomical location.

In certain embodiments, the garment improves athletic performance.

In certain embodiments, the poly elastic strap is configured to relieve all tension in the garment when the wearer is standing with correct postural alignment and in certain embodiments, the garment allows a full range of motion for the wearer.

In certain embodiments, the garment can be sewn into another garment. In certain embodiments, the garment allows for ease of breathing and a comfortable fit.

In certain embodiments, the garment assists the wearer in muscular tension rebalance. In certain embodiments, the garment assists the wearer for shoulder muscle rebalance, shoulder rehabilitation, shoulder recovery, and/or shoulder training. In certain embodiments, the garment assists the wearer with scapula rebalance.

In certain embodiments, the garment includes woven fabric. In certain embodiments, the garment includes knitted fabric. In certain embodiments, the garment includes antimicrobial properties. In certain embodiments, the garment includes moisture wicking properties. In certain embodiments, the garment includes ultra-violet (UV) ray blocking properties. In certain embodiments, the garment front is detachable from the garment back.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
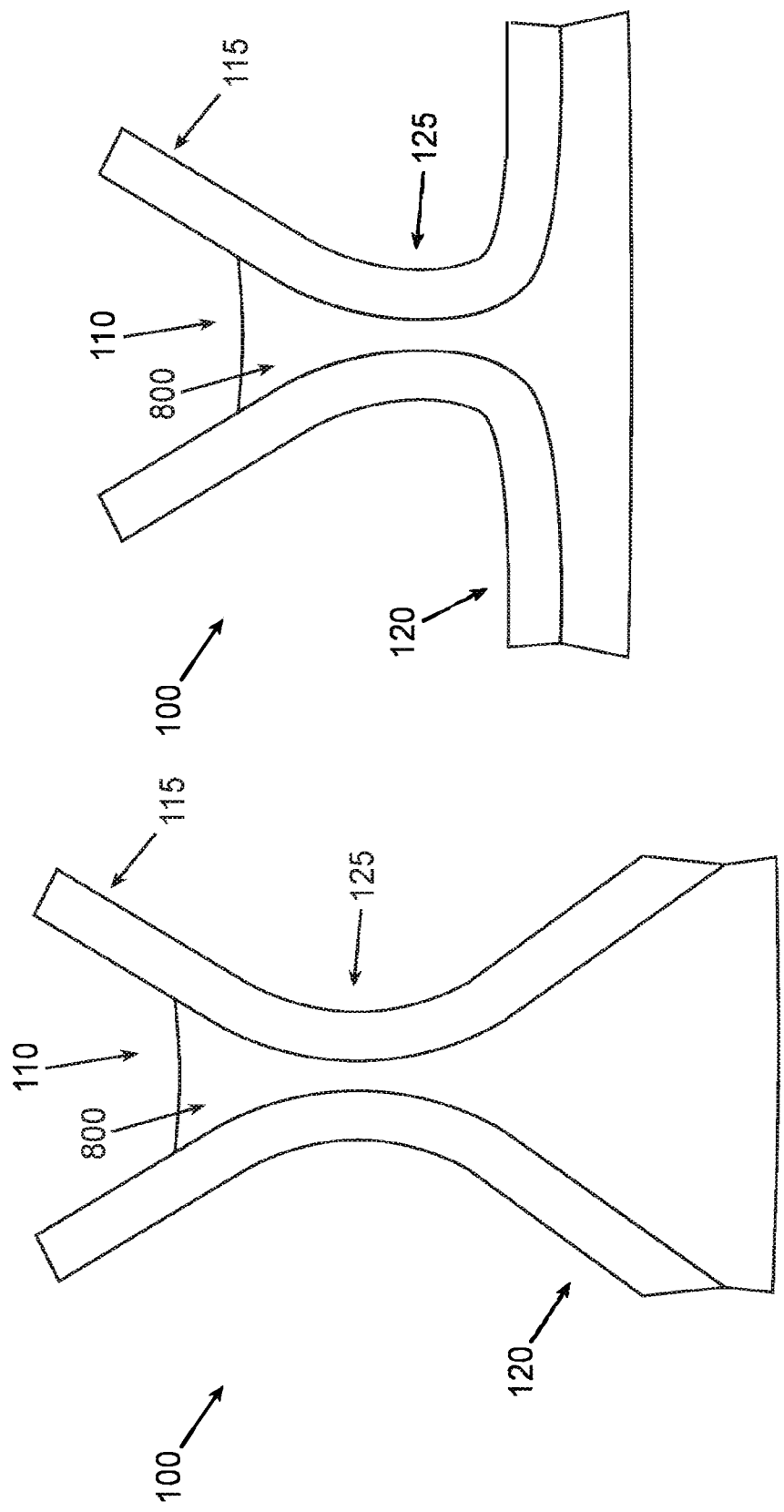
FIGS. 1A 1B are close-up views of the opposing-C on the back of the bra according to an embodiment of the invention.

This application incorporates by reference U.S. patent application Ser. No. 16/024,881 entitled POSTURE, PERFORMANCE, RECOVERY GARMENT DEVICE SYSTEM. The contents of this application are incorporated by reference herein in its entirety.

The present invention is a wearable device manufactured garment that accounts for the limitations of the currently made LYCRA® spandex fiber garments and utilizes a unique fabric design and construction method that involves both an Opposing-C or Center C design as well as a poly elastic strap that contributes horizontal stretch to achieve proprioceptive postural correction and muscle rebalance. The other components include one or more upper straps, a chest band, expansion elastic, and side seams. The garment is designed to be worn by a user in the form of a bra, thus mitigating the issue of an unsightly garment that users wouldn't want to wear as their only layer. The bra is also customizable, fashionable, and breathable.

Branded as the Posture Recovery and I FEEL GOOD— this is a device that accounts for all three namesake items in its title: (1) proprioceptively correcting a wearer's posture, (2) allowing for better recovery via correction of poor posture habits and challenging body habitus, and (3) Feeling good upon wearing the bra. The garment also improves upon previous posture garments through its flexible nature, namely the ability to act as a garment addendum device, i.e. the bra can be sewn into any existing garment or come pre-packaged into a new garment fresh off the production line. It achieves this flexibility while also solving the issues of shoulder restriction and non-breathability through allowing a full range of motion. The construction of prior garments did not allow for forward range of motion due to the 'FIG. 8' or 'horse collar' nature of the loop, which was closed and had an inelastic seam. The garment, in comparison without it, narrows the distance between shoulder blades at least mm, previously unable to be accomplished by any prior art postural bra.

One of the posture correcting features of the garment, the 'Opposing-C' or 'Center C', is created using woven, no-stretch, nylon and TENCEL® lyocell fiber spandex. In an alternative embodiment, the 'Opposing-C' or 'Center C', is created using a two-way stretch material. In certain embodiments, the posture correcting bra comes with a much more limited amount of space to create this Center C design. Given this limited space, the bra cannot rely on the length of the fabric, as the shirt does, to create the force that will provide correct postural alignment. Accordingly, the nature of the fabric and design must change to achieve proper postural tension with a smaller C shape, the details of which are highlighted below. In certain embodiments, the bra uses fabric that is moisture wicking, anti-microbial, contains UV protection, and, unlike the LYCRA® spandex fiber of competitors, breathable.

The woven nature of the C-shaped fabric provides a style benefit, which is the elimination of the typical, unsightly seam construction of previous flat-lock construction posture correction garments. As mentioned above, the C shape is limited in length due to the smaller nature of the bra versus a shirt. To make up for the limited length of fabric, there is a unique nylon bonding that is added to the C shape to provide structural rigidity. This nylon bonding creates a heavier fabric that supplements the poly elastic vertical strap in the center of the spine, providing postural proprioception at the appropriate rates of tension.

The garment also allows for customizability, as the front part of the bra is fully detachable from the back, which provides additional optionality in the form of variable support for both front and back. The front part of the bra comes in full coverage, flat front, or triangle cut, accounting for both style purposes and variation in needed support (larger vs. smaller breasts). The interchangeable nature of the bra does not change the amount of pressure that the bra back provides to the shoulders and thoracic for proprioceptive correction, thus adding a unique benefit without the drawbacks of a lesser product. The attachment points are on the upper straps and the side seams.

The upper straps end in interlocking hooks that can be used to detach the front and back; however, there are no lower straps, but rather side seams included on both the front and back of the bra to provide support to the curve of the back (i.e. allowing forward and backward movement such as bending). The side seams and poly elastic vertical strap are connected to a lower chest band that all combines to further contribute to proprioceptive posture correction by pulling the bra towards the anterior of the wearer's body. To help achieve comfort, there is a highly flexible, accordion style elastic band sewn into the chest band and located beneath the armpit of each arm. This elastic band limits 360-degree compression that is uncomfortable for the wearer. Furthermore, the bra of the present invention is easier to put on than traditional bras since the expansion panels are not just one piece and instead open up the rib cage, thus allowing the wearer to breathe more easily. By contrast, traditional bras are one piece, providing uncomfortable 360-degree compression.

The main posture correcting feature of the bra is the poly elastic strap with horizontal stretch and mesh lining in the back and in the C strap, with the tailored elastic pulling all the tension towards the center of the spine and helping pull the shoulder blades into proper alignment. Specifically, the poly elastic strap achieves posture correction through a proprioceptive manner that involves creating a parallel amount of tension in the body's anatomical musculature, helping active and passive scapular motion of retraction and protraction into better anatomical alignment as well as improved rib cage flexibility and ease of expansion. Once the patient is in correct postural alignment, the bra automatically relieves all tension in the garment. Thus, the wearer will barely notice the device once the wearer has achieved the muscle memory of correct posture.

In addition, the poly elastic strap and the Opposing C construction, while allowing for a full range of motion and shoulder mobility, actually prevents hyperextension with an over hand motion. It protects hyperextension of the rotator cuff, thus preventing damage of the shoulder and spinal muscles.

The inventive garment includes an Opposing-C or Center-C configuration as well as a Mesh-poly elastic strap that provides horizontal stretch to achieve proprioceptive postural correction and muscle rebalance. Other elements include one or more upper straps, a chest band, expansion elastic, and side seams. The garment is intended and configured to be worn by a user in the form of a bra, thus mitigating the issue of an unsightly garment that users wouldn't want to wear as their only layer. The garment is also customizable, fashionable, and breathable.

Benefits of the inventive garment include: proprioceptively correcting a wearer's posture by shoulder blades retraction; hence narrowing the distance between them, improving wearers' performance and motion generated power via better posture and form; and allowing for better recovery via correction of poor posture habits. The garment also improves upon previous posture garments through its flexible nature, namely the ability to act as a garment addendum, i.e. the bra can be sewn into an existing garment or come pre-packaged into a newly produced garment. The inventive garment provides flexibility and allows full range of motion while also solving issues of shoulder restriction and non-breathability. The construction of prior-art garments does not allow for a forward range of motion due to 'FIG. 8' or 'horse collar' configurations with closed and inelastic seams.

One element of the inventive posture correcting garment is an "opposing-C" or "center C" configuration using woven, no-stretch nylon and TENCEL® lyocell fiber spandex, with embedded single or double lining mesh design.

The nature of the inventive C-shaped fabric provides a style benefit, which is the elimination of the typical, unsightly seam construction of previous flat-lock construction posture correction garments. As mentioned above, the inventive C-shape is shorter due to the smaller nature of the inventive garment bra versus the known corrective shirts. To make up for the limited length of fabric, the unique and inventive nylon bonding added to the C shape provides structural rigidity. This inventive nylon bonding creates a heavier fabric that supplements the poly elastic vertical strap at the center of the spine, providing postural proprioception with appropriate amounts of tension.

The inventive garment also allows for customization, as a front portion of the garment or bra is fully detachable from a back portion providing additional wear options in the form of variable support for both garment front and back. The front portion of the garment may be configured for full coverage, flat front, or triangle cut, accounting for both style purposes and variation in needed pectoral support to include a range of chest and/or breast sizes. The interchangeable nature of the garment does not change or impact the amount of support or pressure provided by the garment to the shoulders and thorax for proprioceptive correction, thus adding a unique benefit without the drawbacks of a lesser product. The attachment points of the inventive garment via the upper straps and side seams.

Upper straps may include interlocking hooks used to detach the front portion and back portion. Additionally, the inventive garment lacks lower straps and rather includes side seams on both the front portion and back portion to correct and/or support to the curve of the back while still allowing forward and backward movement of the spine such as during bending or rising from a seated position. The side seams and poly elastic vertical strap(s) are connected to a lower chest band that all together further contributes to proprioceptive posture correction by pulling the garment towards the anterior of the wearer's body. To help achieve comfort, the inventive garment includes highly flexible, accordion style elastic sewn into a chest band and located beneath the armpit of each arm. This elastic chest band limits 360-degree compression that may be uncomfortable for the wearer. Furthermore, the inventive garment is easier to put on than traditional corrective garments because the expansion panels open up the rib cage, thus allowing the wearer to breathe more easily and naturally. By contrast, typically known traditional corrective garments are one piece and exert uncomfortable 360-degree compression.

A main posture correcting feature of the inventive garment is the pretensioned poly elastic strap-mesh with horizontal see saw tension-stretch in the back exerting specific and tailored elastic tension towards the center of the spine and moving the scapula closer to each other, and into better alignment. The mesh-strap also tension the scapula into improved anatomical alignment, leading to better shoulder posture. Specifically, the poly elastic strap achieves posture correction through a proprioceptive manner that involves creating a parallel amount of tension in the body's anatomical musculature. The inventive garment positions and augments the scapular rotator muscles among others, to provide a pull that naturally assists the wearer into scapula retraction for correct postural alignment. After some usage, the wearer barely notices the garment once the wearer has achieved the muscle strength for and muscle memory of correct posture.

Additionally, the mesh-poly elastic strap and opposing-C configuration of the inventive garment allows for a full range of motion and shoulder mobility; and prevents hyperextension with an over hand motion, prevents hyperextension of the rotator cuff, and thus preventing damage of the subscapularis, infraspinatus, teres major and minor, and supraspinatus. While this hyperextension is prevented, pronation, supination, flexing, and extending are not limited.

The C-shaped straps are cut to specific lengths and shapes as well as made from a specific fabric with the desired stretch property. In one or more embodiments, the first and second C-shaped straps are constructed to be about 1-2 inches wide. For example, the width of the straps may range between about 0.5-2.5 inches. This width of the C-shaped straps allows a retraction force sufficient to effectively retract the scapula and provide comfort to the wearer. In one or more embodiments, the first and second straps are made of a stretchy material, such as a 2-way stretch material. Power mesh lining can be single or double layers in the C straps or the entire back panel or front panel or both front and back panels.

The first and second C-shaped straps may each be divided to an upper section and a lower section. In one or more embodiments, the first strap comprises a first strap upper section and a first strap lower section. In one or more embodiments, the second strap comprises a second strap upper section and a second strap lower section. The upper and lower sections of the C-shaped straps attached to each other via a horizontal middle seam.

In one or more embodiments, the upper C-shaped strap sections connect to the chest portion of the bra. In one or more embodiments, the upper C-shaped sections pass over the top of the shoulder at the acromioclavicular (AC) joint, allowing forward and backward movement. In use, the upper C-shaped sections may extend over the shoulder and terminate at about the middle of the back of a wearer. The upper C-shaped sections may terminate at about, just below about, or just above about the C7-T4 vertebrae of a wearer's spine. In an embodiment of the invention, the upper C-shaped sections usually terminate at about the T-5-T12 vertebrae of a wearer's spine. In one or more embodiments, the upper C-shaped sections overlay a length of the rhomboids and/or upper trapezius. In one or more embodiments, the upper C-shaped sections lay flat across the upper trapezius and terminate at the rhomboids. Such design and configuration of the herein disclosed bra, and consequently position of the straps and sections thereof along the posterior muscles contributes to the proprioception. The C-shaped straps, when overlaying those certain muscle groups stimulate awareness.

In one or more embodiments, the lower sections of the first and second C-shaped straps continue the "C" shape and provide the function of lifting the scapula towards the posterior spine. In one or more embodiments, the lower C-shaped sections start at the middle of the spine, at approximately the T4-T8 vertebrae and terminate at about, or along a length of the mid serratus. Such positioning of the upper C-shaped sections provides expansion to the ribcage and opens the diaphragm upon inhalation.

The garment device further includes a poly elastic strap that provides horizontal tension and sits between the first C-shaped strap and the second C-shaped strap. The poly elastic strap is specifically shaped and sized to mirror the void left between the two opposing C-shaped straps and presents an hourglass shape.

In certain embodiments, the posterior poly elastic strap may comprise "no stretch" nylon and/or TENCEL® lyocell fiber spandex. The poly elastic strap may be manufactured from an elastic material. In certain embodiments, the posterior poly elastic strap may comprise a two-way stretch fabric. Optionally, the poly elastic strap comprises one or more of nylon, TENCEL® lyocell fiber and spandex. In one or more embodiments, the mesh-poly elastic strap comprises between about 30% and about 90% nylon. In one or more embodiments, the poly elastic strap comprises between about 10% and about 30% TENCEL® lyocell fiber. In one or more embodiments, the poly elastic strap comprises between about 5% and about 40% spandex. In one or more embodiments, the poly elastic strap comprises about 80% nylon, about 10% TENCEL® lyocell fiber, and about 10% spandex. In one or more embodiments the combination synthetic or non-synthetic fabric can all be used.

Optionally, the mesh-poly elastic strap includes a plurality of variable tension poly elastic straps disposed one above the other. For example, the bra may comprise three or more, four or more, or five or more horizontal variable tension poly elastic straps. In one or more embodiments, the variable tension poly elastic straps are arranged horizontally, one above the other. Optionally, the poly elastic straps are evenly spaced apart. Further optionally, the variable tension poly elastic straps constructed in an X-shape configuration. In one or more embodiments, the bra comprises three horizontal variable tension poly elastic straps and an X-shaped poly elastic strap configuration, wherein the horizontal poly elastic straps disposed above the X-shaped poly elastic straps.

In certain embodiments, in use, the mesh-poly elastic straps between a location proximate the nucha and down to the center of the back of a wearer. In certain embodiments, in use, the poly elastic straps lay along, and/or aside the scapula, from top to bottom.

In certain embodiments, the mesh-poly elastic straps are provided when maximally stretched, i.e., in a pre-tensioned state. As used herein the term "pre-tensioned state" refers to fabrics being already stretched when sewed to a garment. The fabrics can be sewed when stretched already to their maximal pretensioned level.

Optionally, the mesh-poly elastic strap can include one or multiple configuration, either a pretensioned first horizontal poly elastic strap or adding a second horizontal poly elastic strap. The poly elastic straps are disposed one above the other, forming a first upper poly elastic strap and a second lower poly elastic strap. The first upper poly elastic strap may comprise a two-way stretch fabric and may be disposed between the upper sections of the C-shaped first strap and second strap. The second lower poly elastic strap may comprise a two-way stretch fabric and may be positioned between the lower sections of the C-shaped first and second straps. In one or more embodiments, the upper poly elastic strap affords a horizontal orientation and pulls the first and second C-shaped upper strap sections. Such elasticity of the upper poly elastic strap allows full range of motion and accomplishes the proprioceptive "pull" between the shoulder blades, mimicking the contraction of the rhomboids. The wearer can "remember" such contraction and automatically reacts by retracting the shoulders. Further, the tension on the poly elastic and C-shaped straps, allows proper anatomical position of the shoulders.

In one or more embodiments, the lower poly elastic strap retracts the lower sections of the C-shaped straps towards the center of the spine (i.e., towards the T6-T8 vertebrae). Such retraction can expand tight ribcage allowing for an increased movement of the diaphragm. The poly elastic strap also aids in the proprioception of proper anatomy by encouraging a neutral posture.

In one or more embodiments, the bra further includes a mesh layer provided underneath the poly elastic strap portion and configured to provide tension and comfort to the wearer. Various types of fabric materials are contemplated and can be used as the mesh layer in the herein disclosed bra. For example, the mesh body may be made from materials chosen from the group consisting of nylon, spandex, cotton, polyester, chiffon, denim, lace, leather, wool, or a combination thereof. Mesh layer can be single or multiple pending on body habitus, age, and activity desired.

In one or more embodiments, the elastic strap is pretensioned and can be of various lengths in a pretensioned configuration from super angle of scapula to inferior angle of scapula. The PPR Bra narrows R and L scapula distance (with arms on the side of the body and at a resting position) at a minimum of 5 millimeter.

In one or more embodiments, the posture Bra always narrows R and L scapula distance and can be in the range between 5 mm to 25 mm).

In one or more embodiments, the pretensioned elastic straps can be configured on the exterior or the interior on the user's back.

In one or more embodiments, the pretensioned elastic straps are not visualized on the exterior by a user.

The herein disclosed bra effects vertical and/or horizontal scapular retraction towards the spine and/or allows narrowing the distance between the left and right scapula. The herein disclosed bra successfully affords narrowing the distance between the left and right scapula. As measured empirically, utilizing the Scapula Lennie test, the bra presents, in average, about 11 mm (range of between about 5 mm and about 25 mm) narrowing of the distance between the left and right scapula. Thus, in certain embodiments, the herein disclosed bra effects at least about 5 mm narrowing of the distance between the left and right scapula.

FIG. 1A and FIG. 1B depict the inventive garment (100) back portion including an opposing-C or C-shaped posterior central portion (110) with a first strap (115) connecting to the posterior C-shaped portion (110) at or near the shoulder of a wearer. The inventive garment (100) includes a second strap (120) connecting to the posterior C-shaped central portion (110) at or near the center of the wear's back. The posterior central portion (110) includes a poly elastic strap (800) and is configured to expand and contract.

Figure 8:
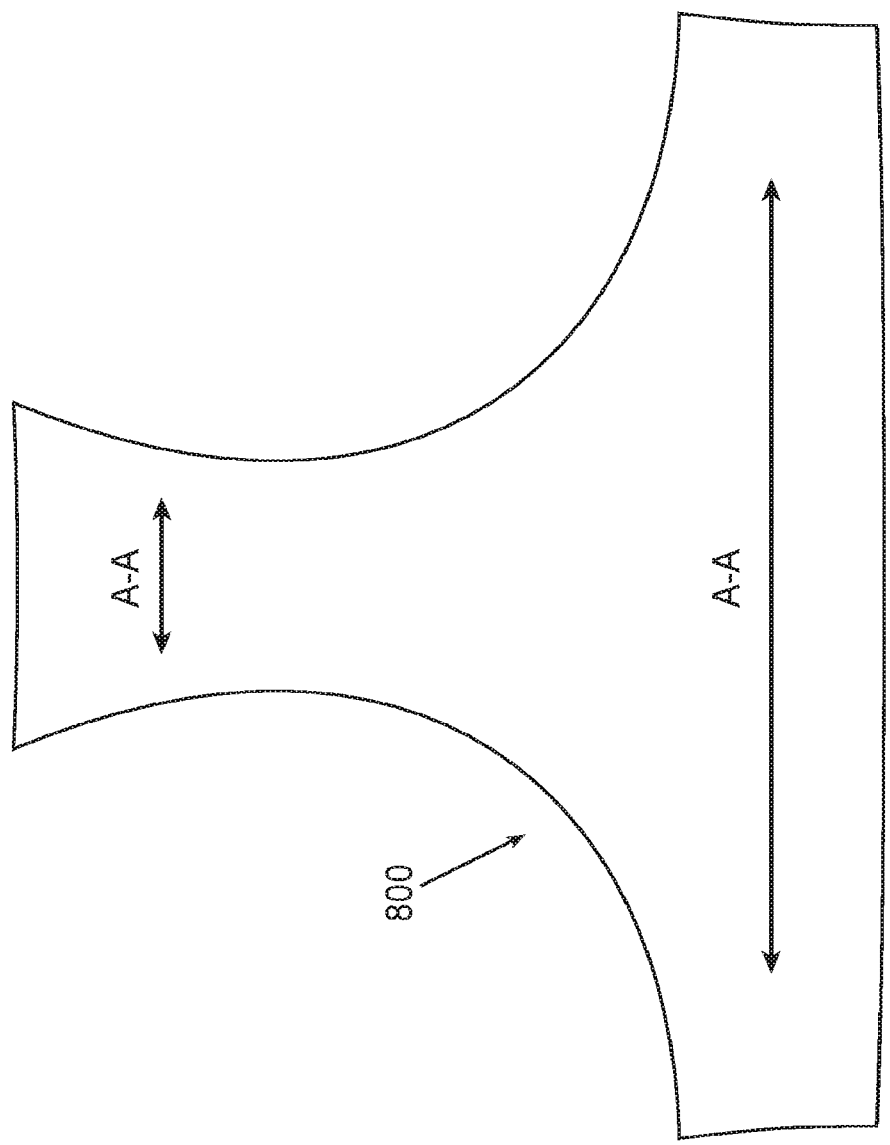
FIG. 8 is a view of the poly elastic strap of an embodiment of the invention.

As shown in FIG. 8, poly elastic strap (800) is configured to stretch in a horizontal direction A-A In certain embodiments, the first strap and at the second strap (115, 120) may connect to the posterior C-shaped central portion (110) fabric material itself In certain embodiments, the first strap (115) and the second strap (120) connect to the side seams, which in turn connect to the poly elastic strap. The poly elastic strap and the side seams connect to the chest band (see FIG. 3A).

In certain embodiments, the posterior C-shaped central portion (110) may comprise 80% nylon, 10% TENCEL® lyocell fiber, and 10% spandex resulting in a non-stretchable and woven fabric. As set forth above, for the posterior C-shaped central portion (110) to proprioceptively correct a wearer's posture with the limited amount of fabric; the posterior C-shaped central portion (110) is preferably of a weight and rigidity that once the first strap and second strap (115, 120) adjusted, exert a pull or force wherein the posterior C-shaped central portion (110) is approximately pressed anteriorly against the wear's back. One method to achieve this desired structural rigidity without causing discomfort to the wearer is to include nylon bonding (125) which also provides for a "heavier feel" to the wearer (see FIG. 2).

In other embodiments, the spine is no longer acting as a natural anchor point, since the poly elastic strap is now in-between the two Cs, and so the poly elastic strap acts as the anchor point to naturally correct alignment. In this embodiment, the two C-shaped portions of the straps are used along with the poly elastic strap to correct a wearer's posture.

Figure 2:
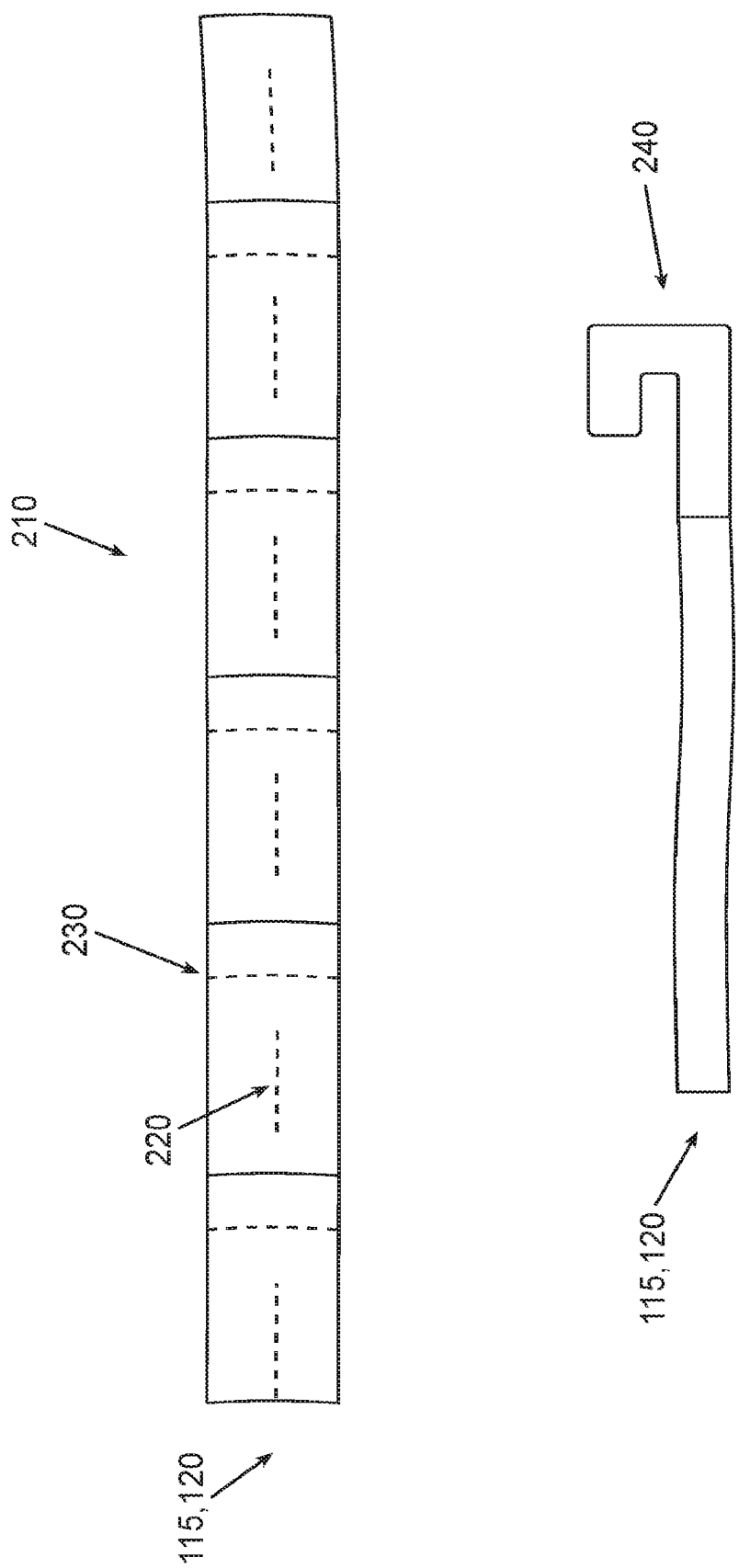
FIG. 2 is a view of the adjustable and detachable strap that links the front portion of the garment to the back portion of the bra according to an embodiment of the invention.

The front portion (FIG. 4) of the inventive garment (100) may can be removed from the back portion (FIG. 1 and FIG. 3A) using an adjustable strap or modular body. Referring to FIG. 2, separation of the front portion (FIG. 4) from the back portion (FIGS. 1 and 3) may be achieved via a plurality of fabric pockets (210) built into the first and second straps (115, 120) and including nylon loops (220, 230) which are under the fabric pockets (210). A hook (240) may terminate the ends of the first and second straps (115, 120) and insert into the nylon loops (220, 230). Inserting the plastic hooks (240) into the nylon loops (220, 230) secures the inventive garment (100) front portion (FIG. 4) and back portion (FIGS. 1 and 3) together at a desired tension. In certain embodiments, the hook (240) is made of plastic, a polymer, nylon or other material that has sufficient rigidity.

FIG. 3A and FIG. 3B depict the posterior back portion of the inventive garment (100), including the posterior C-shaped central portion (110). The first strap (115) may be made of two-way stretch woven poly spandex to provide more flexibility. First strap (115) may stretch approximately 1 to 1 inches in length providing comfort but still proprioceptively correcting the wearer's posture. The first strap (115) is configured to pass over the wear's shoulder at the acromioclavicular joint and to pull the shoulder of the wearer to the anterior and placing the scapula in the proper anatomical location. The elastic chest band (310) may comprise a two-way stretch fabric for a more comfortable fit. Combined with the poly elastic strap, the chest band creates an anterior pull that "opens up" the ribcage, thus making breathing easier when compared to known tight and overly compressive posture shirts; thus, providing a more comfortable fit.

In certain embodiments, the elastic chest band (310) is attached to the poly elastic strap and the side seams.

Figure 3:
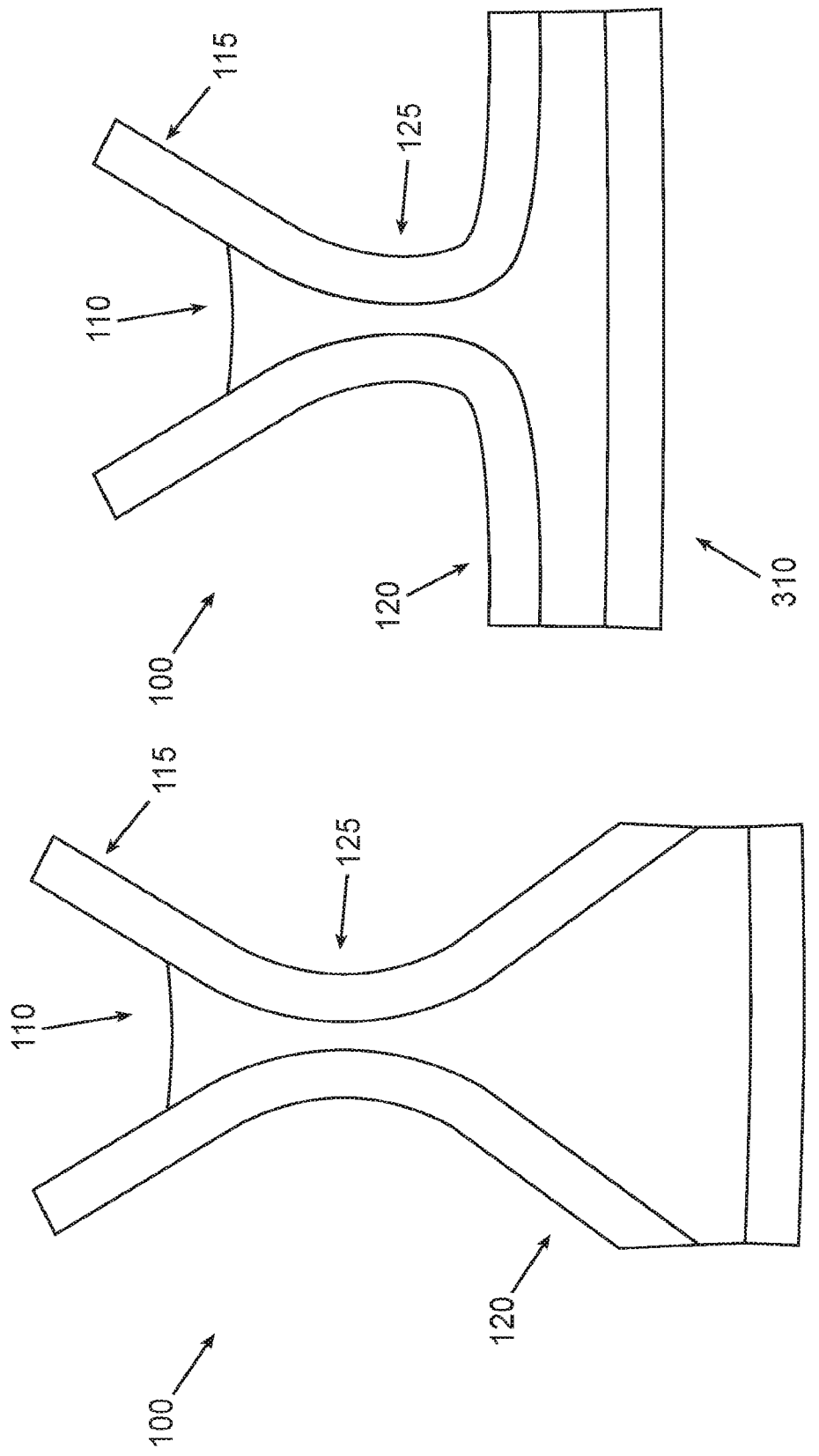
FIGS. 3A and 3B is a view of the posterior of the bra according to an embodiment of the invention.
Figure 4:
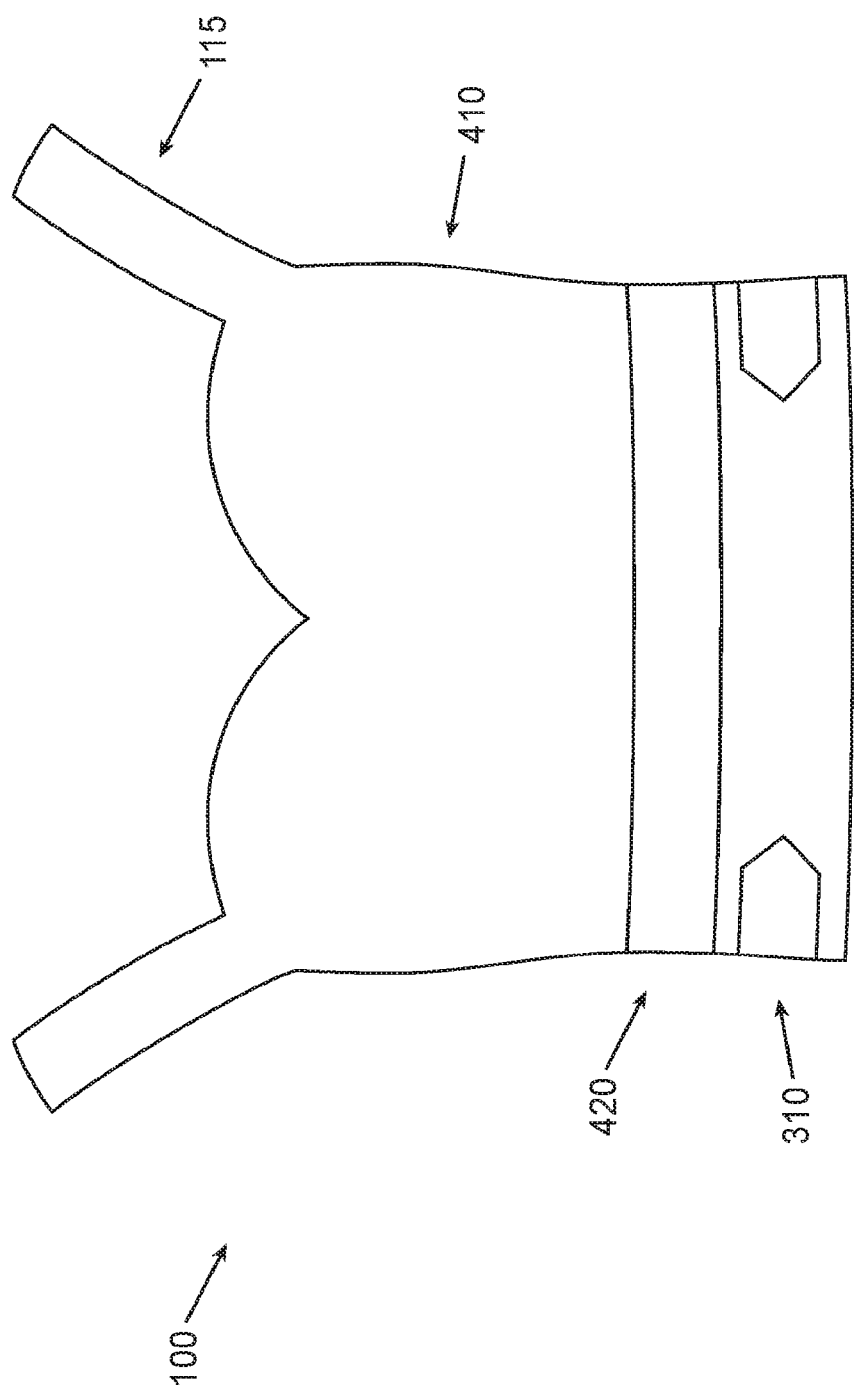
FIG. 4 is a depiction of the anterior of the bra of FIG. 3A.

FIG. 4 depicts a detachable front portion of the inventive garment (100), which allows users to purchase a single back portion (FIGS. 1 and 3) and a plurality of front portions (FIG. 4) based on their needs and style and support preferences. A garment front portion may be provided in full front, flat front, or triangle cut (410) to accommodate both male and female wearers of varying body shapes and sizes. The garment front portion may be "cut and sew" or seamless without affecting functionality, since the bulk of the postural proprioceptive work is achieved by the poly elastic strap (800) and the posterior C-shaped central portion (110) anchored at garment back portion (FIGS. 1 and 3). The bottom of the garment front portion may include sheathed elastic comprising an elastic band that is covered by another material (see FIG. 6) having less resistance than the second strap (120) of the garment back portion (FIGS. 1 and 3); thus, providing additional comfort. The bra's (100) first strap (115) may connect at the top of the garment back portion via fabric pockets (210) and nylon loops (220, 230) as described and depicted in FIG. 2. Optionally, an underbreast support system (420) may be included to provide comfort and support to the wearer.

Figure 5:
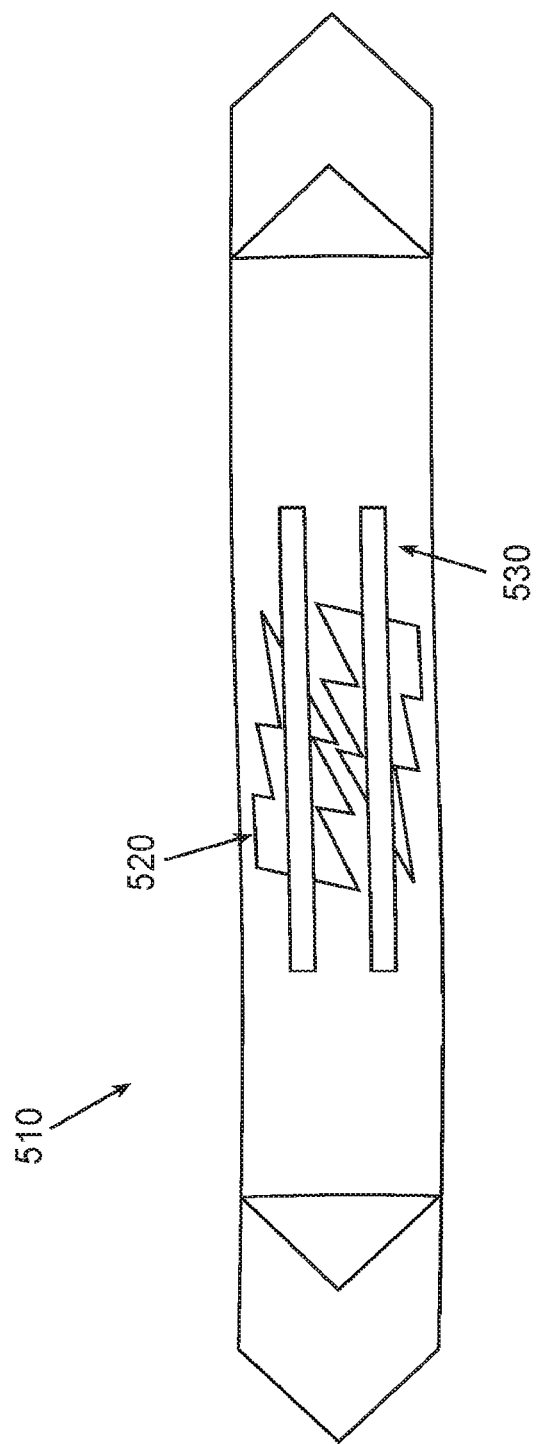
FIG. 5 is a close-up view of the expansion elastic of the straps of the bra of FIG. 3A.

Referring to FIG. 5, expansion elastic (510) is shown in a close-up depiction of the elastic chest band (310). The expansion elastic (510) may be highly flexible, accordion style elastic, sewn into the chest band (310) and limits uncomfortable 360-degree compression to the wearer. The expansion elastic (510) also allows the garment to be donned more easily by the wearer. The chest band (310) is folded and creased (520) at the area where the expansion elastic in-sewn; and may include an expansion limiter (530).

Figure 6:
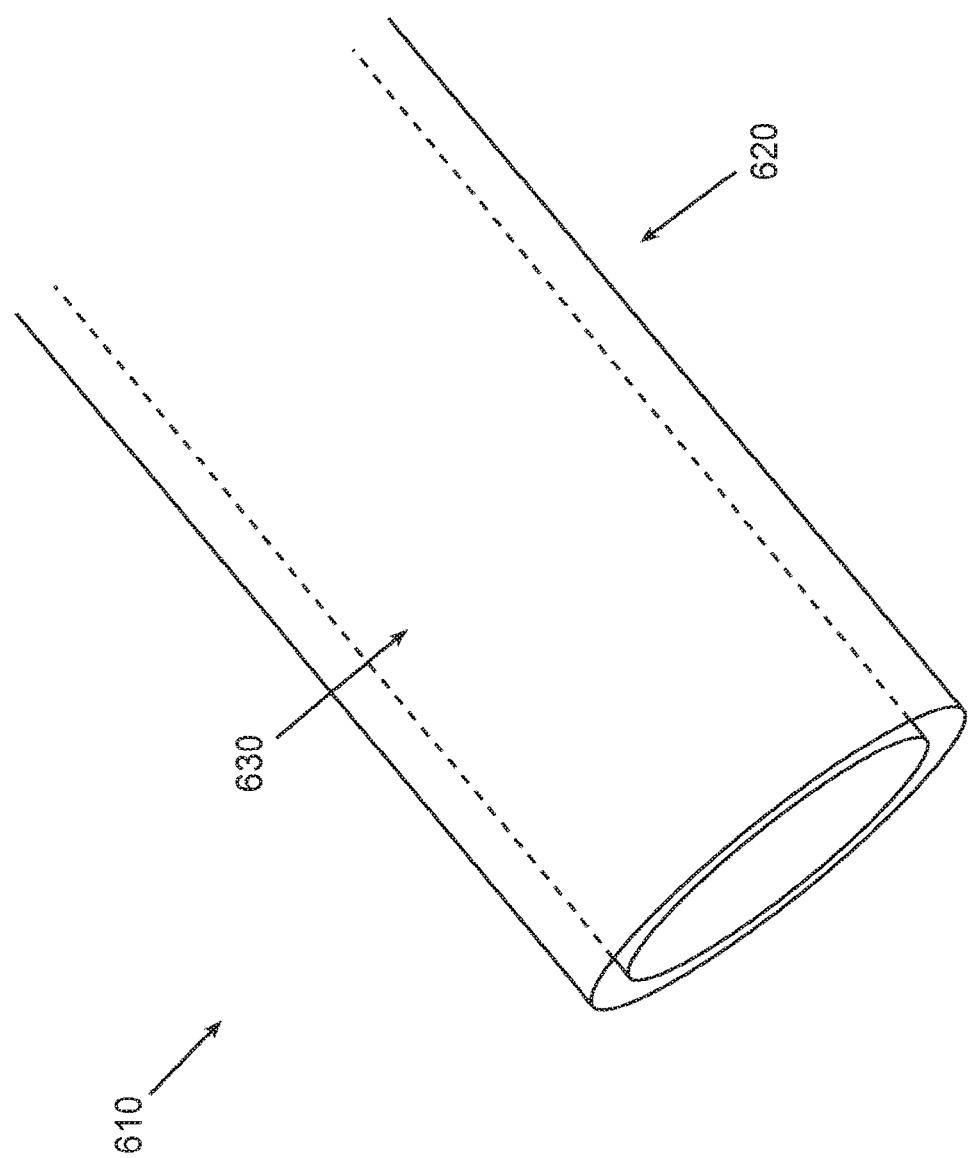
FIG. 6 is a close-up view of the sheathed elastic and strap of the bra of FIG. 3A.

Referring to FIG. 6, the sheathed elastic (610) integral to the first and second straps (115, 120) is depicted. The first strap (115), the second strap (120), and elastic chest (310) straps may all include a sheathed elastic, that includes a fabric casing or sheath (620) covering an elastic strap (630). In the case of the elastic chest band (310), the expansion elastic (610) may be integral to or added to the chest strap or band (310).

Figure 7:
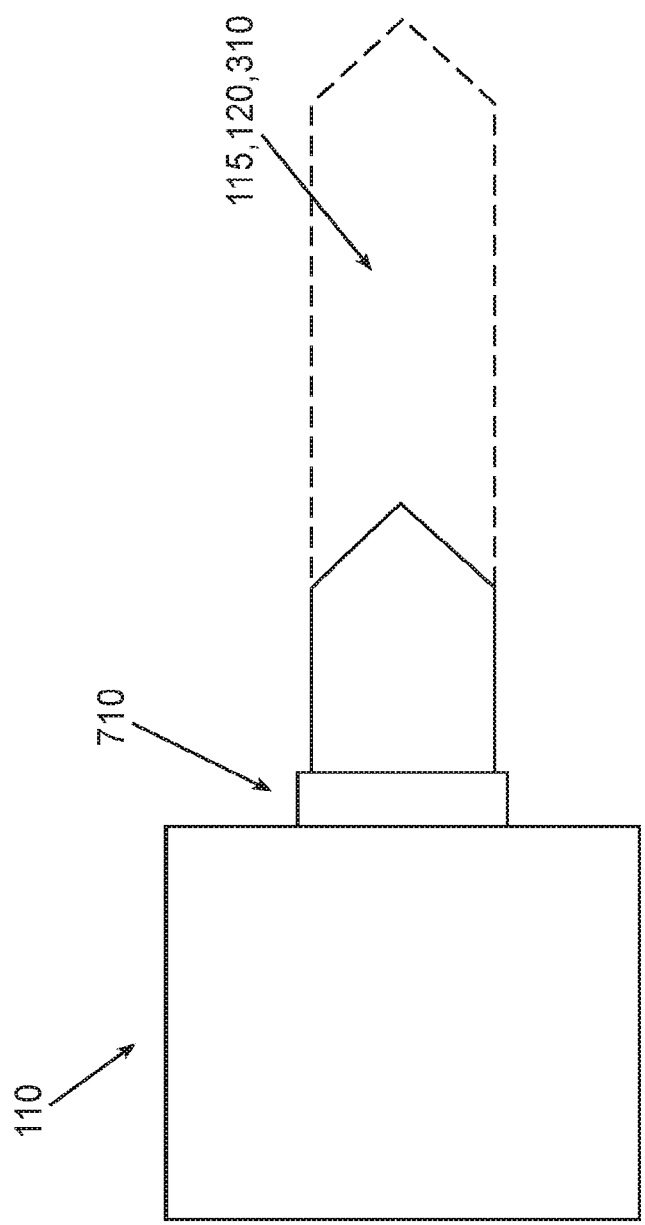
FIG. 7 is a close-up view of the connection points of the opposing-C to the straps of the bra of FIG. 3A.

Referring to FIG. 7, the inventive garment (100) connection and adjustment of the posterior C-shaped central portion (110) to and with the at first and second straps (115, 120) becomes clear. FIG. 7 depicts a close-up view of a connection point between the posterior C-shaped central portion (110) and the straps. Two connection points may be utilized—upper left and upper right. The posterior C-shaped central portion (110) may be connected via a nylon polymer loop (710) to the sheathed elastic (610) of the straps (115, 120, 310), as discussed and depicted in FIG. 6. The straps (115, 120, 310), may be passed through the nylon polymer loop (710) on the posterior C-shaped central portion (110) and attached via Velcro® or other adjustment and securing system or method.

Figure 9:
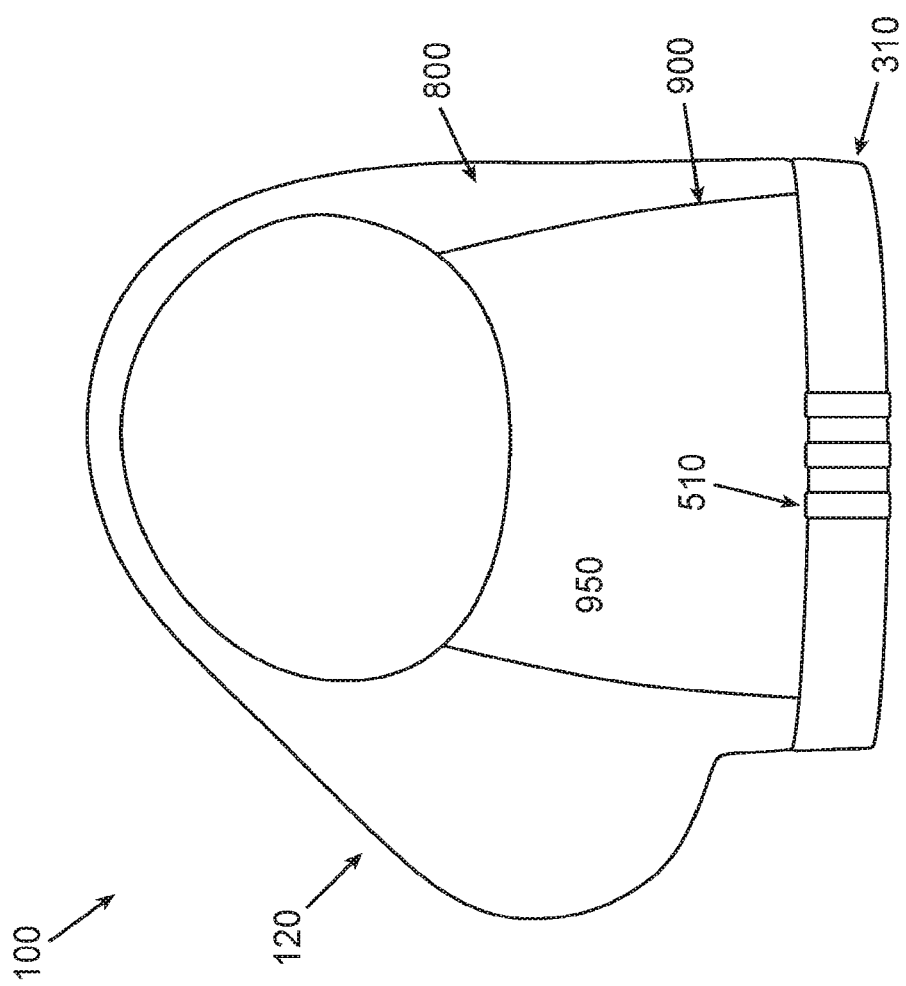
FIG. 9 is a side view of the bra of FIG. 3A.
Figure 10:
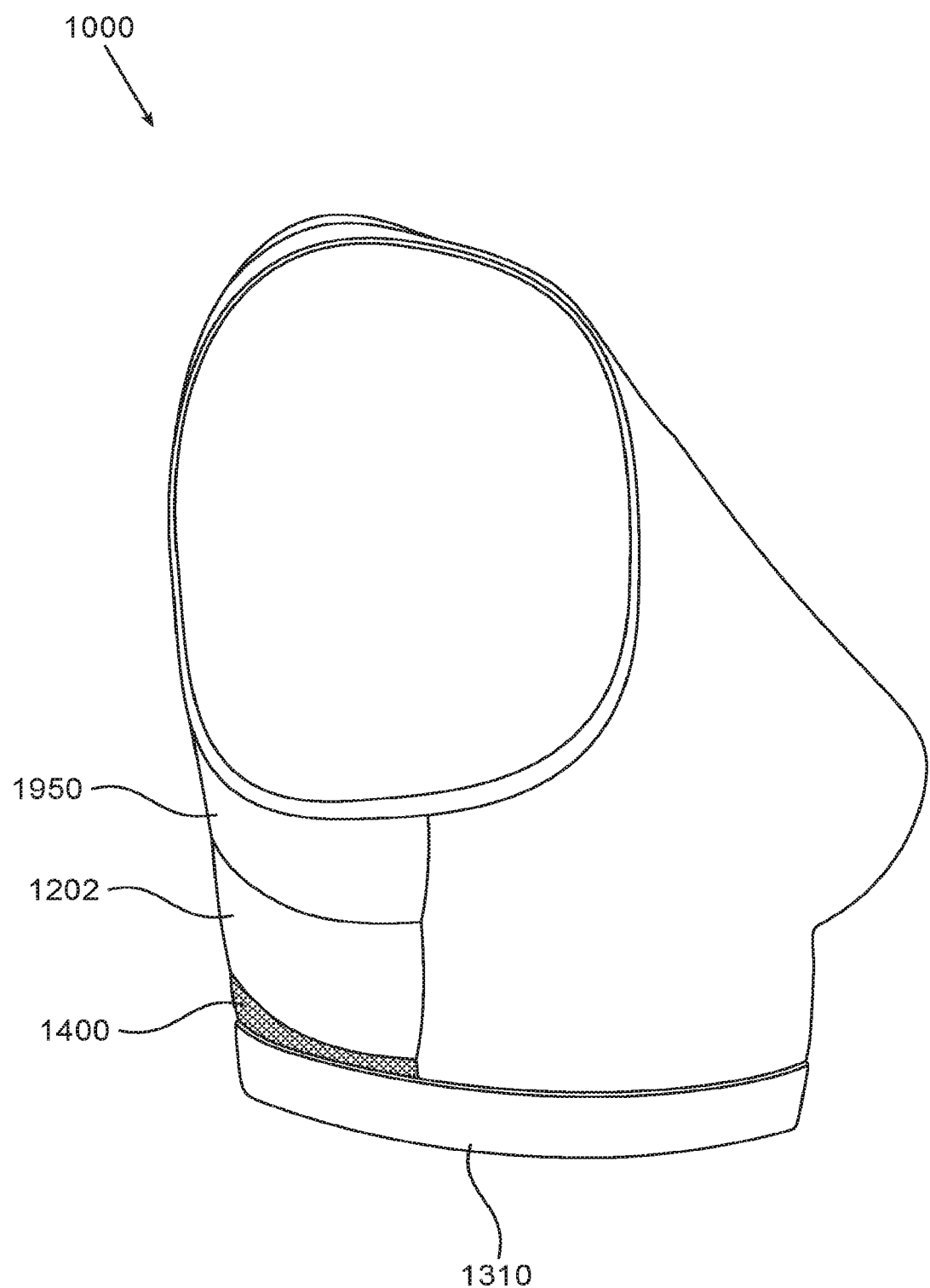
FIG. 10 is a side view of a bra with a first upper poly elastic strap and a second lower poly elastic strap, according to an embodiment of the invention.
Figure 11:
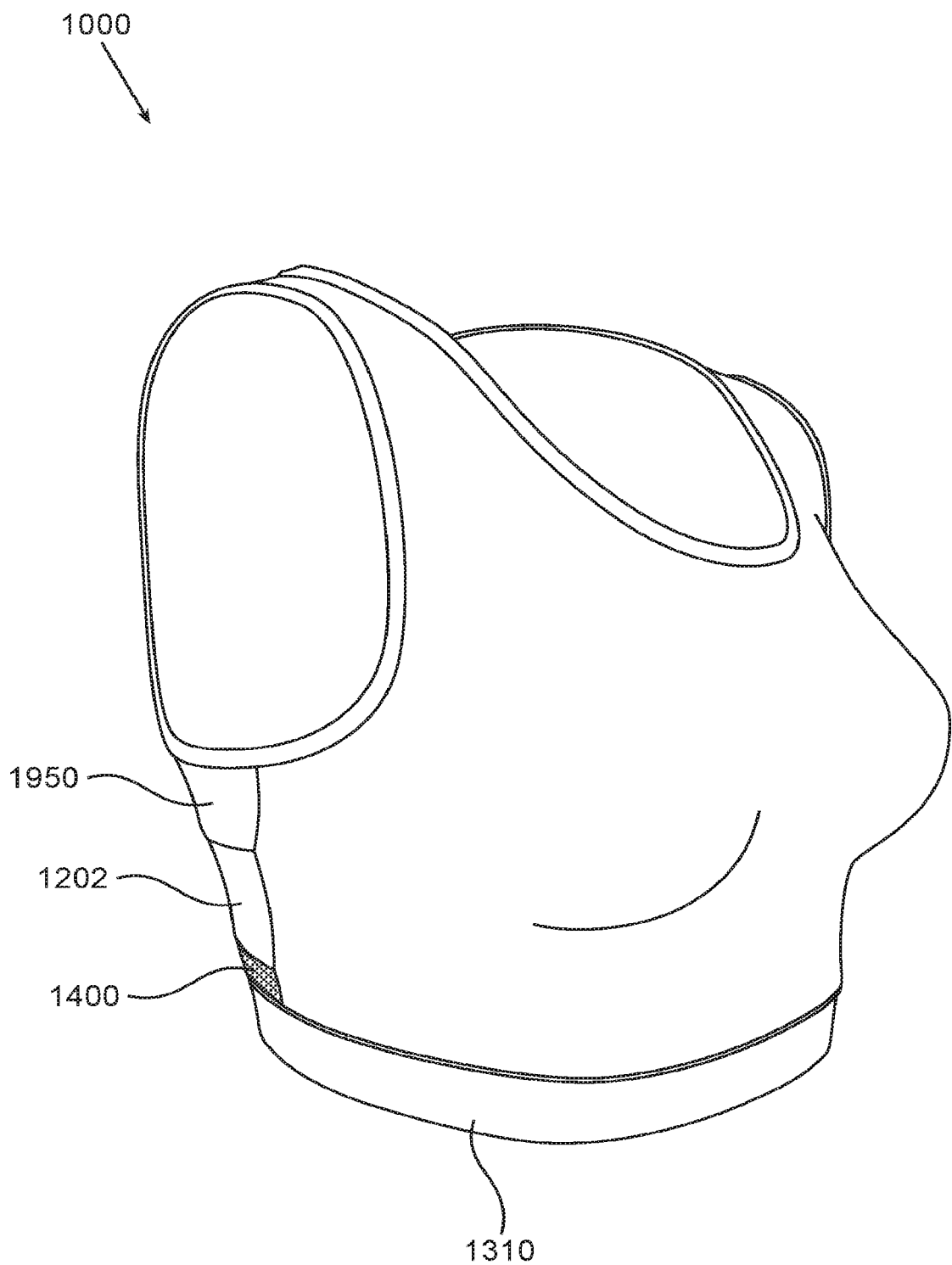
FIG. 11 is a perspective front view of the bra of FIG. 10.
Figure 12:
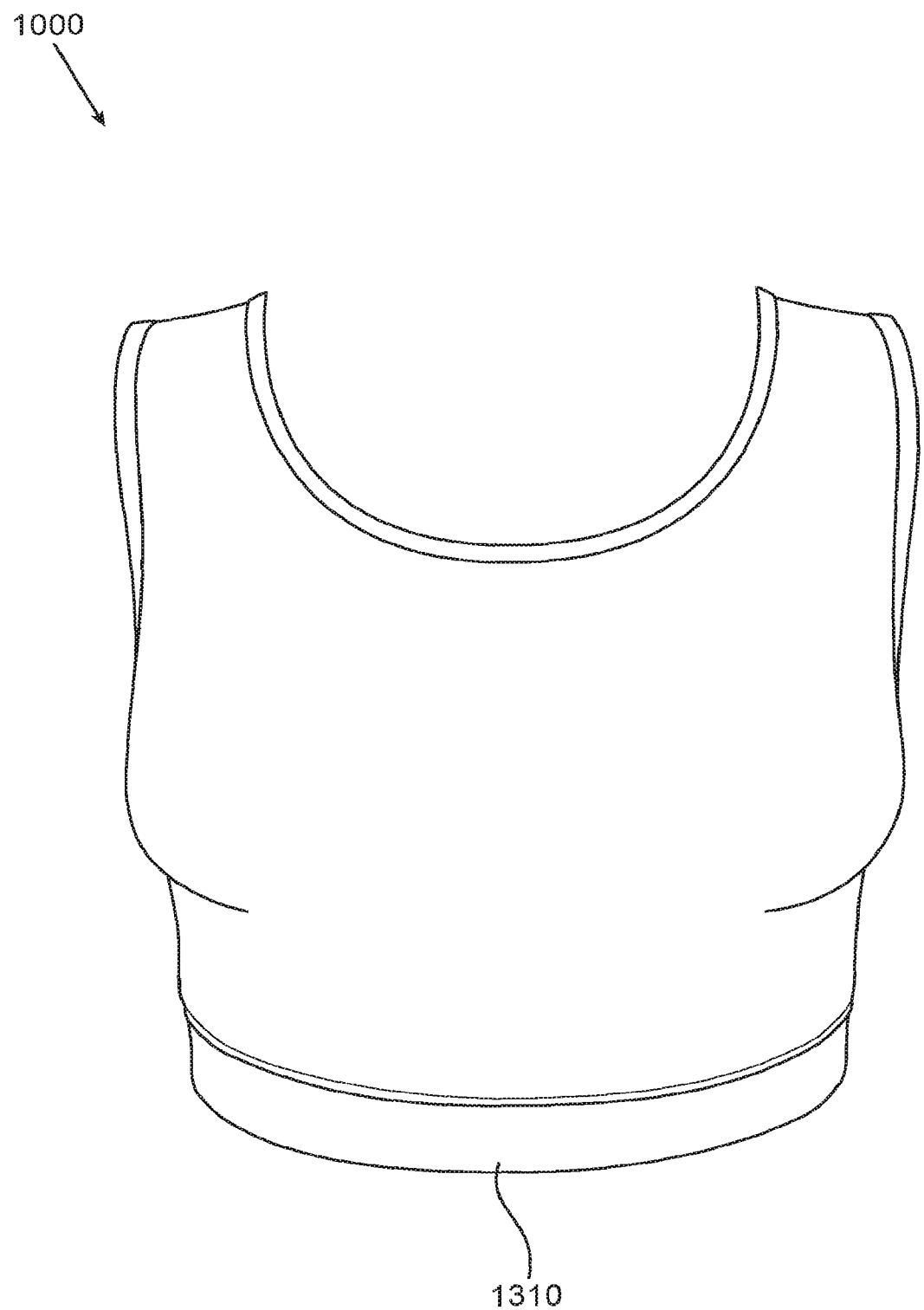
FIG. 12 is a depiction of the anterior of the bra of FIG. 10.
Figure 13:
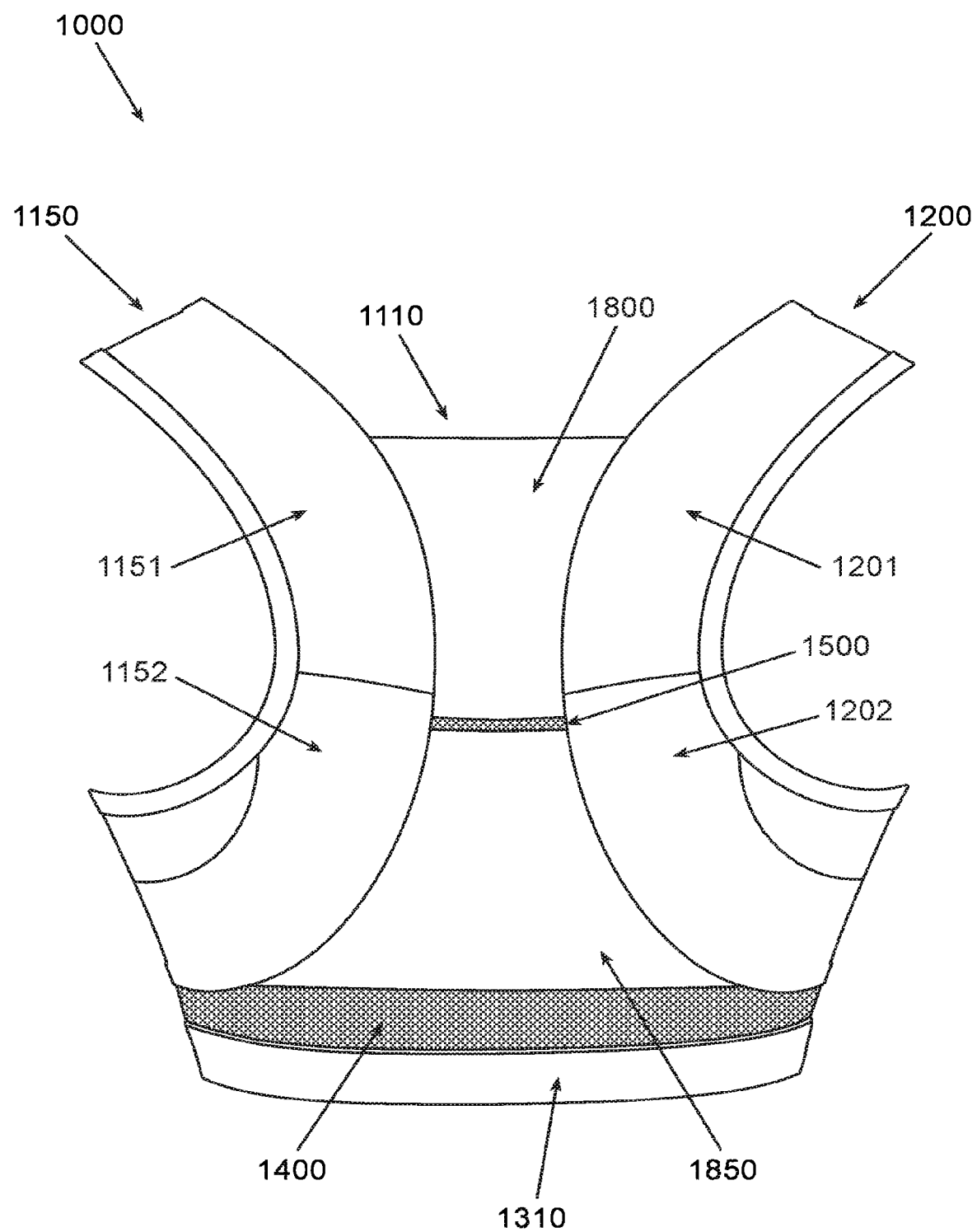
FIG. 13 is a depiction of the posterior of the bra of FIG. 10.
Figure 14:
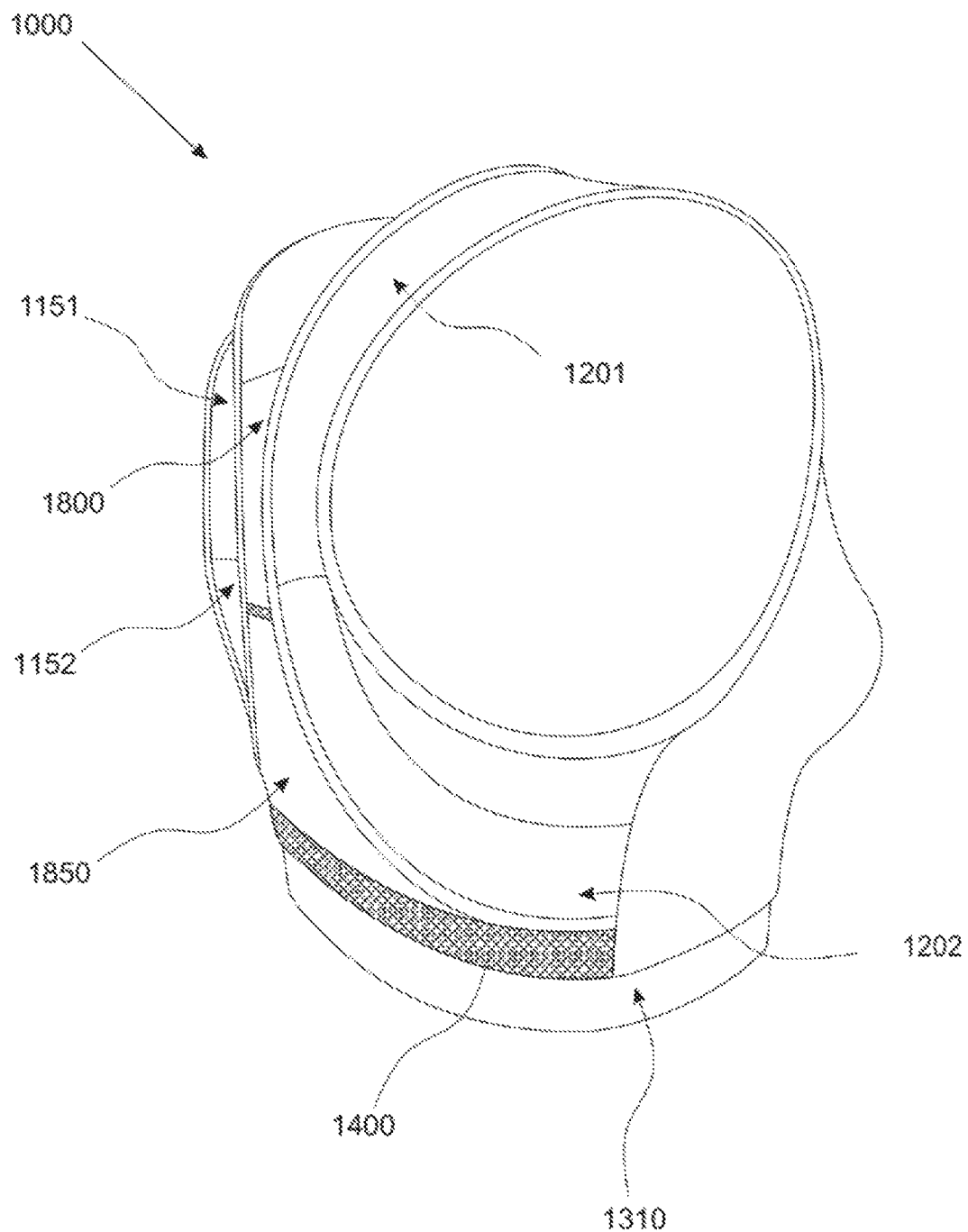
FIG. 14 is a perspective back view of the bra of FIG. 10.
Figure 15:
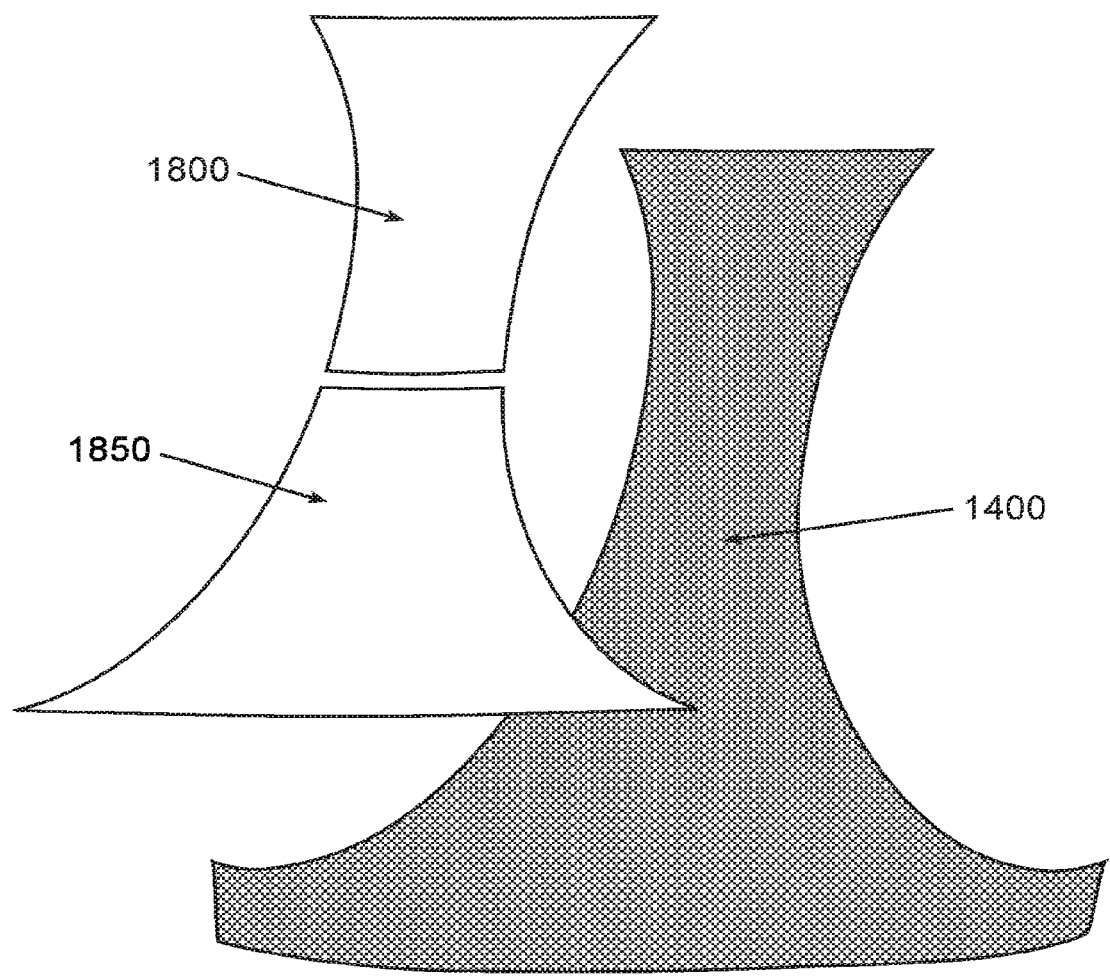
FIG. 15 is an exploded view of the mesh layer and the first and second poly elastic straps of the bra of FIG. 10.

Referring to FIG. 8, the poly elastic strap (800) is shown. The poly elastic strap (800) is configured to stretch in a horizontal direction A-A In certain embodiments, the first strap and at the second strap (115, 120) may connect to the posterior C-shaped central portion (110) fabric material itself Referring to FIG. 9, a side view of FIG. 3A is shown. FIG. 9 shows a view from the left-hand side of the bra (100). As shown, the bra (100) has a strap (120) shown on the anterior portion of the bra (100). At the posterior portion, poly elastic strap (800) is shown connected to side seam (900). Also shown is chest band (310). The side (950) of the bra (100) made of fabric is also shown.

Referring to FIGS. 10-15, another exemplary bra 1000 is shown. Bra 1000 includes a C-shaped first strap (1150) and a C-shaped second strap (1200) forming an opposing-Coran approximate X-shape configuration with the opposing C's that form the shape never touching or intersecting across the back of a wearer. The first strap (1150) includes an upper C-shaped strap section 1151 and a lower C-shaped strap section (1152). The second strap (1200 includes an upper C-shaped strap section 1201 and a lower C-shaped strap section (1202). A posterior poly elastic central portion (1100) includes an upper first poly elastic strap (1800) and a lower second poly elastic strap (1850) configured to expand and contract and further to stretch the C-shaped straps (1150, 1200) in a horizontal direction A-A The first poly elastic strap (1800) and second poly elastic strap (1850) are spaced apart such that a slit 1500 extends between the first and second poly elastic straps (1800, 1850). A mesh layer (1440), either single or multiple, is provided underneath the poly elastic central portion (1100) or added to the C-strap or the entire front panel or back panel or in the entire bra. Mesh layer 1440 is made from a synthetic or non-synthetic fabric providing tension, and comfort to the wearer. Bra 1000 further includes a chest band (1310) which may be similar to chest band 310 of bra (100).

Figure 16:
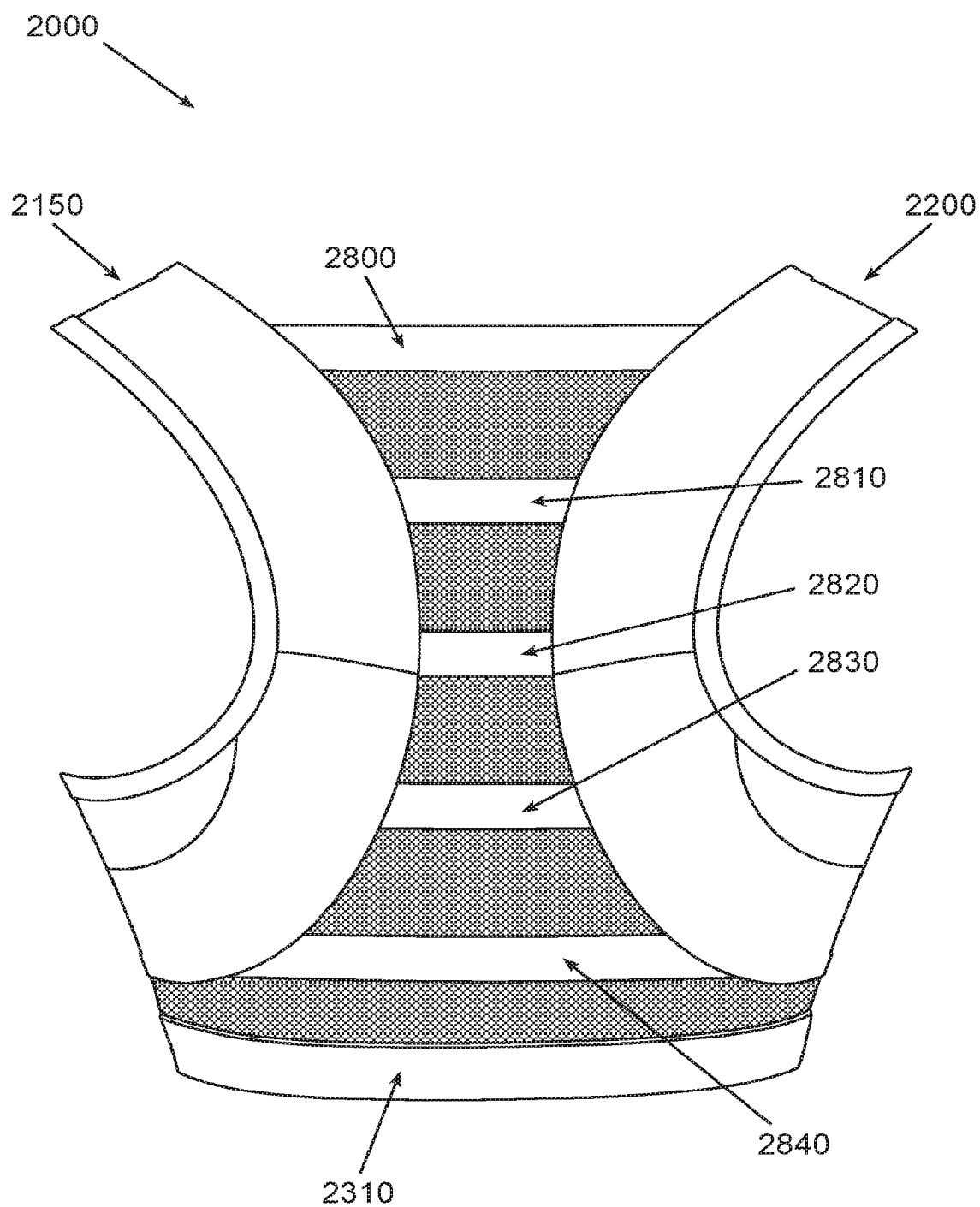
FIG. 16 is a posterior view of a bra comprising a plurality of horizontal variable tension poly elastic straps, according to an embodiment of the invention.

Referring to FIG. 16, another exemplary bra 2000 is shown. Bra 2000 is similar to bra 1000 with the exception that it has five poly elastic straps (2800, 2810, 2820, 2830, 2840). The straps (2800, 2810, 2820, 2830, 2840) are disposed horizontally one above the other. To maximize narrowing the distance between the right scapula and the left scapula, the straps are disposed within the bra such that, in use, the straps lay along, and/or aside the scapula from top to bottom.

Figure 17:
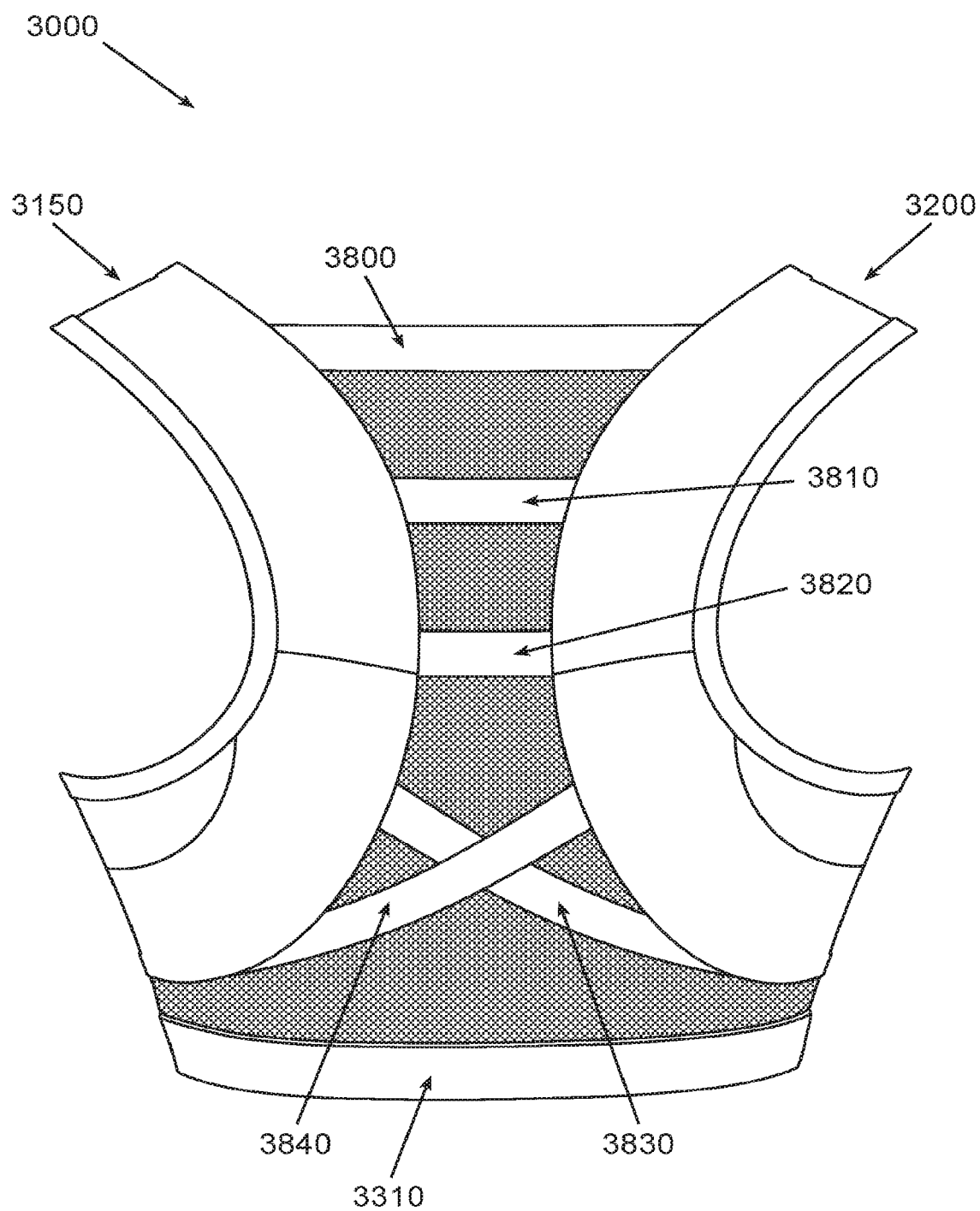
FIG. 17 is a posterior view of a bra comprising a plurality of horizontal variable tension poly elastic straps and straps constructed with an approximate X-shape configuration, according to an embodiment of the invention.

Referring to FIG. 17, another exemplary bra 3000 is shown. Bra 3000 is similar to bra 2000 with the exception that the bottom most straps (3830, 3840) are disposed in an X-shaped configuration, extending diagonally from respective lower sections of C-shaped straps (3150, 3200) and affording additional tension force to thereby retract the scapula. In the embodiment shown in FIG. 17, bottom most straps (3830, 3840) cross along the midline of the bra. To further maximize narrowing the distance between the right scapula and the left scapula, the straps are disposed within the bra such that, in use, the straps lay along, and/or aside the scapula from top to bottom. As shown, there may be a plurality of open slots formed between the elastic straps; for example, a first slot extends vertically between the first and second elastic straps, and a second slot extends vertically between the second and third elastic straps.

It is contemplated that many and various systems and methods may be used to secure the front and back portions of the garment using the inventive straps (115, 120, 310); including but not limited to: buttons, snaps, zippers, hook and loop, hole and lace, or Velcro® type fasteners; and combinations thereof.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

What is claimed is:

1. A posture correction bra, comprising:
   a front portion;
   a back portion;
   a first strap, the first strap configured in an approximate C-shape including a two-way stretch fabric, the first strap attached to the front portion of the posture correcting bra at one end of the first strap;
   a second strap, the second strap configured in an approximate C-shape including a two-way stretch fabric, the second strap attached to the front portion of the posture correcting bra at one end of the second strap;
   at least two horizontal spaced apart straps that provide horizontal tension and extend between the first strap and the second strap; and
   at least one mesh layer provided underneath the at least two horizontal spaced apart elastic straps,
   wherein an upper section of the first strap is configured to provide a greater force upon a wearer than a lower section of the first strap, and wherein an upper section of the second strap is configured to provide greater force upon the wearer than a lower section of the second strap,
   wherein the bra further includes a pair of side seams connecting the front portion to the back portion along respective left and right sides of the bra, the pair of side seams further connecting the front portion to the lower section of the first strap and the lower section of the second strap, and
   wherein the first strap and the second strap each include a middle seam connecting the respective upper section and the respective lower section of the first and second straps.

2. The bra of claim 1, wherein the at least two horizontal spaced apart straps are each configured to provide horizontal tension between the C-shaped first and second straps.

3. The bra of claim 1, wherein the C-shape of the first strap and the C-shape of the second strap together form an approximate X-shape configuration, wherein the opposing C-shapes do not touch or intersect across a back of the wearer when the bra is worn.

4. The bra of claim 1, wherein the C-shape of the first strap and the C-shape of the second strap oppose one another, such that the first strap and the second strap each have the C-shape facing away from a center of the wearer's back when the bra is worn.

5. The bra of claim 1, wherein the first strap and the second strap each have a width within the range of between about 1 inch and about 4 inches.

6. The bra of claim 1, wherein each upper section is configured to extend from a base of a neck of the wearer to a location proximate at least one thoracic vertebra of a spine of the wearer.

7. The bra of claim 6, wherein each lower section is configured to extend from said location proximate the at least one thoracic vertebra to a location proximate an inferior angle of a scapula of the wearer.

8. The bra of claim 1, wherein the bra is configured to correct a wearer's posture by narrowing the distance between the wearer's left and right scapula by at least 5 mm.

9. The bra of claim 1, wherein the bra is configured to be integrated to a secondary bra via at least one integrated intersection.

10. The bra of claim 1, wherein said front portion further includes an inner mesh lining.

\* \* \* \* \*